(12) United States Patent
Pantazis et al.

(10) Patent No.: US 9,352,055 B2
(45) Date of Patent: May 31, 2016

(54) FUNCTIONALIZATION OF AND USE OF FUNCTIONALIZED SECOND HARMONIC GENERATING NANOPROBES

(71) Applicant: California Institute of Technology, Pasadena, CA (US)

(72) Inventors: Periklis Pantazis, Oberwil (CH); Jelena Culic-Viskota, Chandler, AZ (US); William P. Dempsey, The Woodlands, TX (US); Scott E. Fraser, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/850,661

(22) Filed: Sep. 10, 2015

(65) Prior Publication Data

US 2016/0051705 A1    Feb. 25, 2016

Related U.S. Application Data

(62) Division of application No. 13/683,975, filed on Nov. 21, 2012, now Pat. No. 9,221,919.

(60) Provisional application No. 61/562,289, filed on Nov. 21, 2011.

(51) Int. Cl.
*A61K 49/00* (2006.01)
*G01N 33/58* (2006.01)
*C07K 17/14* (2006.01)

(52) U.S. Cl.
CPC ......... *A61K 49/0093* (2013.01); *A61K 49/0063* (2013.01); *C07K 17/14* (2013.01); *G01N 33/588* (2013.01)

(58) Field of Classification Search
CPC .................................................. A61K 49/0093
See application file for complete search history.

(56) References Cited

U.S. PATENT DOCUMENTS

| 5,538,898 A | 7/1996 | Wickramasinghe et al. |
| 5,952,180 A | 9/1999 | Ju |

(Continued)

FOREIGN PATENT DOCUMENTS

| WO | 2004106896 A2 | 12/2004 |
| WO | 2008140584 A2 | 11/2008 |

(Continued)

OTHER PUBLICATIONS

International Search Report for International Application No. PCT/US2007/085407, completed Oct. 20, 2008, mailed Oct. 31, 2008, 2 pgs.

(Continued)

*Primary Examiner* — Paul Dickinson
(74) *Attorney, Agent, or Firm* — KPPB LLP

(57) ABSTRACT

Functionalized second harmonic nanoprobes for imaging samples and a method of using such probes to monitor the dynamics different processes using a variety of imaging techniques are provided. The functionalized second harmonic generating (SHG) nanoprobes are comprised of various kinds of nanocrystalline materials that do not possess an inversion symmetry and therefore are capable of generating second harmonic signals that can then be detected by conventional two-photon microscopy, and are provided with functional surface modifications that allow for targeted imaging of a variety of biological and non-biological processes and structures such as cell signaling, neuroimaging, protein conformation probing, DNA conformation probing, gene transcription, virus infection and replication in cells, protein dynamics, tumor imaging and cancer therapy evaluation and diagnosis as well as quantification in optical imaging.

20 Claims, 25 Drawing Sheets

(56) References Cited

U.S. PATENT DOCUMENTS

| | | | |
|---|---|---|---|
| 6,624,915 | B1 | 9/2003 | Kirkpatrick et al. |
| 7,009,700 | B2 | 3/2006 | Dubois et al. |
| 7,679,079 | B1 | 3/2010 | Marks et al. |
| 7,813,016 | B2 | 10/2010 | Pu et al. |
| 7,993,891 | B2 | 8/2011 | Roitman et al. |
| 8,945,471 | B2 | 2/2015 | Pantazis et al. |
| 2003/0148391 | A1 | 8/2003 | Salafsky et al. |
| 2004/0023415 | A1 | 2/2004 | Sokolov et al. |
| 2004/0146460 | A1 | 7/2004 | Salafsky |
| 2005/0025422 | A1 | 2/2005 | Magnusson et al. |
| 2005/0186565 | A1 | 8/2005 | Malak |
| 2005/0267345 | A1 | 12/2005 | Korgel et al. |
| 2006/0056468 | A1 | 3/2006 | Dantus et al. |
| 2006/0228725 | A1 | 10/2006 | Salafsky |
| 2006/0289115 | A1 | 12/2006 | Zhao et al. |
| 2010/0233820 | A1 | 9/2010 | Pantazis |
| 2012/0141981 | A1 | 6/2012 | Pantazis et al. |
| 2013/0129628 | A1 | 5/2013 | Pantazis |

FOREIGN PATENT DOCUMENTS

| | | | |
|---|---|---|---|
| WO | 2010/090844 | A2 | 8/2010 |
| WO | 2010090844 | A2 | 8/2010 |
| WO | 2010/090844 | A3 | 11/2010 |
| WO | 2013078410 | A1 | 5/2013 |

OTHER PUBLICATIONS

International Search Report for International Application No. PCT/US2007/085409, completed Oct. 7, 2008, mailed Oct. 10, 2008, 2 pgs.

Written Opinion for International Application No. PCT/US2007/085407, filed Nov. 21, 2007, completed Oct. 20, 2008, mailed Oct. 31, 2007, 7 pgs.

International Search Report and Written Opinion for International Application No. PCT/US2012/066391, completed Feb. 23, 2013, 8 pgs.

Akerman et al., , "Nanocrystal targeting in vivo", PNAS, Oct. 1, 2002, vol. 99, No. 20, pp. 12617-12621.

Alivisatos, "The use of nanocrystals in biological detection", Nature Biotechnology, Jan. 2004, vol. 22, No. 1, pp. 47-52.

Andreoni et al., "Holographic properties of the second-harmonic cross correlation of object and reference optical wave fields", J. Opt. Soc. Am., Jun. 2000, vol. 17, No. 6, pp. 966-972.

Averitt et al., "Linear optical properties of gold nanoshells", J. Opt. Soc. Am. B, Oct. 1999, vol. 16, No. 10, pp. 1824-1832.

Baker et al., "Imaging Brain Activity with Voltage-and Calcium-Sensitive Dyes", Cellular and Molecular Neurobiology, Apr. 2005, vol. 25, No. 2, pp. 245-282.

Bannai et al., "Imaging the lateral diffusion of membrane molecules with quantum dots", Nature Protocols, 2006, vol. 1, No. 6, pp. 2628-2634.

Bastiaens et al., "Fluorescence lifetime imaging microscopy: spatial resolution of biochemical processes in the cell", trends in Cell Biology, Feb. 1999, vol. 9, pp. 48-52.

Billinton et al., "Seeing the Wood through the Trees: A Review of Techniques for Distinguishing Green Fluorescent Protein from Endogenous Autofluorescence", Analytical Biochemistry, 2001, vol. 291, pp. 175-197.

Blanchard et al., "Eliminating membrane depolarization caused by the Alzheimer peptide (A_(1-42, aggr.)", Biochemical and Biophysical Research Communications, 2002, vol. 293, pp. 1204-1208.

Bosnjak et al., "Towards preventive medicine", EMBO reports, 2008, vol. 9, No. 11, pp. 1056-1060.

Braslavsky et al., "Sequence information can be obtained from single DNA molecules", PNAS, Apr. 1, 2003, vol. 100, No. 7, pp. 3960-3964.

Brauns et al., "Complex Local Dynamics in DNA on the Picosecond and Nanosecond Time Scales", Physical Review Letters, Apr. 15, 2002, vol. 88, No. 15, pp. 158101-1-158101-4.

Bruchez, Jr. et al., "Semiconductor Nanocrystals as Fluorescent Biological Labels", Science, Sep. 25, 1998, vol. 281, pp. 2013-2016.

Callender et al., "Fast Events in Protein Folding: The Time Evolution of Primary Processes", Annu. Rev. Phys. Chem., 1998, vol. 49, pp. 173-20.

Campagnola et al., "Second-harmonic imaging microscopy of living cells", Journal of Biomedical Optics, Jul. 2001, vol. 6, No. 3, pp. 277-286.

Campagnola et al., "Second-harmonic imaging microscopy for visualizing biomolecular arrays in cells, tissues and organisms", Nature Biotechnology, Nov. 2003, vol. 21, No. 11, pp. 1356-1360.

Chalfie et al., "Green Fluorescent Protein as a Marker for Gene Expression", Science, New Series, Feb. 11, 1994, vol. 263, No. 5148, pp. 802-805.

Chan et al., "Quantum Dot Bioconjugates for Ultrasensitive Nonisotopic Detection", Science, Sep. 25, 1998, vol. 281, pp. 2016-2018.

Chang et al., "An Efficient Approach to Derive Hydroxyl Groups on the Surface of Barium Titanate Nanoparticles to Improves tis Chemical Modification Ability", Journal of Colloid and Interface Science, 2009, 300-305.

Cheatham, III, "Simulation and modeling of nucleic acid structure, dynamics and interactions", Current Opinion in Structural Biology, 2004, vol. 14, pp. 360-367.

Chen et al., "Protein localization in living cells and tissues using FRET and Flim", Differentiation, 2003, vol. 71, pp. 528-541.

Cohen, "Beyond fluorescence", Nature, Sep. 23, 2010, vol. 467, pp. 407-408.

Cuche et al., "Simultaneous amplitude-contrast and quantitative phase-contrast microscopy by numerical reconstruction of Fresnel off-axis holograms", Applied Optics, Dec. 1, 1999, vol. 38, No. 34, pp. 6994-7001.

Dahan et al., "Diffusion Dynamics of Glycine Receptors Revealed by Single-Quantum Dot Tracking", Science, Oct. 17, 2003, vol. 302, pp. 442-445.

Day et al., "Imaging Molecular Interactions in Living Cells", Molecular Endocrinology, Jul. 2005, vol. 19, No. 7, pp. 1675-1686.

Denk et al., "Two-Photon Laser Scanning Fluorescence Microscopy", Reports, Apr. 6, 1990, vol. 248, No. 4951, pp. 73-76.

Dickson et al., "On/off blinking and switching behaviour of single molecules of green fluorescent protein", Nature, Jul. 24, 1997, vol. 388, pp. 355-358.

Ding et al., "Direct Observation of Protein Folding, Aggregation, and a Prion-like Conformational Conversion", The Journal of Biological Chemistry, Dec. 2, 2005, vol. 280, No. 48, pp. 40235-40240.

Dobson, "The structural basis of protein folding and its links with human disease", Phil. Trans. R. Soc. Lond. B , 2001, vol. 356, pp. 133-145.

Dobson, "Protein folding and misfolding", Nature, Dec. 18-25, 2003, vol. 426, pp. 884-890.

Dombeck et al., "Optical Recording of Fast Neuronal Membrane Potential Transients in Acute Mammalian Brain Slices by Second-Harmonic Generation Microscopy", J. Neurophsiol. 2005, vol. 94, pp. 3628-3636.

Dubertret et al., "In Vivo Imaging of Quantum Dots encapsulated in Phospholipid Micelles", Science, Nov. 29, 2002, vol. 298, pp. 1759-1762.

Dubois et al., "Improved three-dimensional imaging with a digital holography mircoscope with a source of partial spatial coherence", Applied Optics, Dec. 1, 1999, vol. 38, No. 34, pp. 7085-7094.

Dworczak et al., "Electric field induced second harmonic generation (EFISH) experiments in the swivel cell: New aspects of an established method", Phys. Chem. Chem. Phys., 2000, vol. 2, pp. 5057-5064.

Empedocies et al., "Influence of Spectral Diffusions on the Line Shapes of Single CdSe Nanocrystallite Quantum Dots", J. Phys. Chem, 1999, vol. 103, pp. 1826-1830.

Franken et al., "Generation of Optical Harmonics", Physical Review Letters, Aug. 15, 1061, vol. 7, No. 4, pp. 118-120.

Gabor, "A New Microscopic Principle", Nature, May 15, 1948, No. 4098, pp. 777-778.

Gerlich et al., "4D imaging to assay complex dynamics in live specimens", Reviews, Sep. 2003, pp. S14-S19.

(56) References Cited

OTHER PUBLICATIONS

Giepmans et al., "The Fluorescent Toolbox for Assessing Protein Location and Function", Science, Apr. 14, 2006, vol. 312, pp. 217-224.
Gilmanshin et al., "Fast events in protein folding: Relaxation dynamics of secondary and tertiary structure in native apomyoglobin", Proc. natl. Acad. Sci. USA, Apr. 1997, vol. 94, pp. 3709-3713.
Girling et al., "Surface plasmon enhanced SHG from a hemicyanine monolayer", J. Phys. D: Appl. Phys, 1986, vol. 19, pp. 2065-2075.
Greulich, "Fluoresense spectroscopy on single biomolecules", ChemPhysChem, 2005, vol. 6, pp. 2458-2471.
Hadjantonakis et al., "Technicolour Transgenics: Imaging Tools for Functional Genomics in the Mouse", Nature Reviews Genetics, Aug. 2003, vol. 4, pp. 613-627.
Hall, "Advanced sequencing technologies and their wider impact in microbiology", The Journal of Experimental Biology, 2007, vol. 209, pp. 1518-1525.
Harris et al., "Single-Molecule DNA Sequencing of a Viral Genome", Science, Apr. 4, 2008, vol. 320, pp. 106-109.
Hillier et al., "Whole-genome sequencing and variant discovery in c. elegans", Nature Methods, Feb. 2008, vol. 5, No. 2, pp. 183-188.
Jaiswal et al., "Use of quantum dots for live cell imaging", Nature Methods, Oct. 2004, vol. 1, No. 1, pp. 73-78.
Jares-Erijman et al.,"FRET Imaging", Focus on Optical Imaging, Nature Biotechnology, Nov. 2003, vol. 21, No. 11, pp. 1387-1395.
Kim et al., "Mitochondrial permeability transition: a common pathway to necrosis and apoptosis", Biochemical and Biophysical Research Communications, 2003, vol. 304, pp. 463-470.
Kirson et al., "Alternating electric fields arrest cell proliferation in animal tumor models and human brain tumors", PNAS, Jun. 12, 2007, vol. 104, No. 24, pp. 10152-10157.
Krenn et al., "Squeezing the Optical near-Field Zone by Plasmon Coupling of Metallic Nanoparticles", Physical Review Letters, Mar. 22, 1999, vol. 82, No. 12, pp. 2590-2593.
Kubelka et al., "The protein folding 'speed limit'", Current Opinion in Structural Biology, 2004, vol. 14, pp. 76-88.
Lander et al., "Initial sequencing and analysis of the human genome", Nature, Feb. 15, 2001, vol. 409, pp. 860-921.
Leith et al., "Microscopy of Wavefront Reconstruction", Journal of the Optical Society of America, Aug. 1965, vol. 55, No. 8, pp. 981-986.
Leith et al., "Wavefront Reconstruction with Diffused Illumination and Three-Dimensional Objects", Journal of the Optical Society of America, Nov. 1964, vol. 54, No. 11, pp. 1295-1301.
Li et al., "Second harmonic generation in transparent $KTiOPO_4$/ $SiO_2$ nanocomposite glasses prepared by the sol-gel method", Journal of Non-Crystalline Solids, 2000, vol. 261, pp. 273-276.
Lichtman et al, "Fluorescence microscopy", Nature Methods, Dec. 2005, vol. 2, No. 12, pp. 910-919.
Lippincott-Schwartz et al., "Studying Protein Dynamics in Living Cells", Nature, Jun. 2001, vol. 2, pp. 444-456.
Loew, "Potentiometric dyes: Imaging electrical activity of cell membranes", Pure & Appl. Chem, 1996, vol. 88, No. 7. pp. 1405-1409.
Maier et al., "Optical pulse propagation in metal nanoparticle chain waveguides", Physical Review, 2003, vol. B67, pp. 205402-1 thru 205402-5.
Maiman, "Stimulated Optical Radiation in Ruby", Nature, Aug. 6, 1960, vol. 187, pp. 493-494.
Maletic-Savatic et al., "Rapid Dendritic Morphogenesis in CA1 Hippocampal Dendrites Induced by Synaptic Activity", Science, Mar. 19, 1999, vol. 283, pp. 1923-1927.
Margulies et al., "Genome sequencing in microfabricated high-density picolitre reactors", Nature, Sep. 15, 2005, vol. 437, pp. 376-380.
Marquet et al., "Digital holographic microscopy: a noninvasive contrast imaging technique allowing quantitative visualization of living cells with subwavelength axial accuracy", Optics Letters, Mar. 1, 2005, vol. 30, No. 5, pp. 468-470.
McCaig et al., "Controlling Cell Behavior Electrically: Current Views and Future Potential", Physiol. Rev, 2005, vol. 85, pp. 943-978.
Miccio et al, "Direct full compensation of the aberrations in quantitative phase microscopy of thin objects by a single digital hologram", Applied Physics Letters, 2007, vol. 90, pp. 041104-1 thru 041104-3.
Michalet et al., "Quantum Dots for Live Cells, in Vivo Imaging, and Diagnostics", Science, Jan. 28, 2005, vol. 307, pp. 538-544.
Michalet et al., "The Power and Prospects of Fluorescence Microscopies and Spectroscopies", Annu. Rev. Biophys. Biomol. Struct., 2003, vol. 32, pp. 161-182.
Michler et al., "Quantum correlation among photons from a single quantum dot at room temperature", Nature, Aug. 31, 2000, vol. 406, pp. 968-970.
Millar, "Fluorescence studies of DNA and RNA structure and dynamics", Current Opinion in Structural Biology, 1996, vol. 6, pp. 322-326.
Miyawaki, "Innovations in the Imaging of Brain Functions Using Fluorescent Proteins", Neuron, Oct. 20, 2005, vol. 48, pp. 189-199.
Miyawaki, "Visualization of the Spatial and Temporal Dynamics of Intracellular Signaling", Developmental Cell, Mar. 2003, vol. 4, pp. 295-305.
Miyawaki et al., "Dynamic and quantitative Ca2+ measurements using improved cameleons", Proc. Natl. Acad. Sci. USA, Mar. 1999, vol. 96, pp. 2135-2140.
Nie et al., "Probing Single Molecules and Single Nanoparticles by Surface-Enhanced Raman Scattering", Science, Feb. 21, 1997, vol. 275, pp. 1102-1106.
Nirmal et al., "Fluorescence intermittency in single cadmium selenide nanocrystals", Nature, Oct. 31, 1996, vol. 383, pp. 802-804.
Nuccitelli, "A Role for Endogenous Electric Fields in Wound Healing", Curr Top Dev Biol, 203, vol. 58, No. 1, pp. 1-24.
Pantazis et al., "Second harmonic generating (SHG) nanoprobes for in vivo imaging", PNAS, Aug. 17, 2010, vol. 107, No. 33, pp. 14535-14540.
Pantazis et al., "Localized multiphoton photoactivation of paGFP in *Drosophila* wing imaginal discs", Journal of Biomedical Optics, Jul./Aug. 2007, vol. 12, No. 4, pp. 1-1-1-7.
Pedrini et al., "Aberration compensation in digital holographic reconstruction of microscopic objects", Journal of Modern Optics, 2001, vol. 48, No. 6, pp. 1035-1041.
Peleg et al., "Nonlinear optical measurement of membrane ptential around single molecules at selected cellular sites", Proc. Natl. Acad. Sci. USA, Jun. 1999, vol. 96, pp. 6700-6704.
Pelton et al., "Evidence for a diffusion-controlled mechanism for fluorescence blinking of colloidal quantum dots", PNAS, Sep. 4, 2007, vol. 104, No. 36, pp. 14249-14254.
Peter et al., "Imaging molecular interactions by multiphoton FLIM", Biology of the Cell, 2004, vol. 96, pp. 231-236.
Piehler, "New methodologies for measuring protein interactions in vivo and in vitro", Current Opinion in Structural Biology, 2005, vol. 15, pp. 4-14.
Pollok et al., "Using GFP in FRET-based applications", Trends in Cell Biology, Feb. 1999, vol. 9, pp. 57-60.
Pu et al., "Four-dimensional dynamic flow measurement by holographic particle image velocimetry", Applied Optics, Dec. 20, 2005, vol. 44, No. 36, 7697-7708.
Pu et al., "Intrinsic aberrations due to Mie scattering in particle holography", J. Opt. Soc. Am, Oct. 2003, vol. 20, No. 10, pp. 1920-1932.
Qiu et al., "Conducting Polyaniline Nanotubes by Template-Free Polymerization", Macromolecules, 2001, vol. 34, pp. 675-677.
Sandrock et al., "Synthesis and Second-Harmonic Generation Studies of Noncentrosymmetric Gold Nanostructures", J. Phys. Chem. B, 1999, vol. 103, pp. 2668-2673.
Schnars et al., "Direct recording of holograms by a CCD target and numerical reconstruction", Applied Optics, Jan. 19, 1994, vol. 33, No. 2, pp. 179-181.
Selvin, "The renaissance of fluorescence resonance energy transfer", Nature Structural Biology, Sep. 2000, vol. 7, No. 9, pp. 730-734.
Shalaev, "Electromagnetic Properties of Small-Particle Composites", Physics Reports, 1996, 272, pp. 61-137.
Shaner et al., "A guide to choosing fluorescent proteins", Nature Methods, Dec. 2005, vol. 2, No. 12, pp. 905-909.

(56) References Cited

OTHER PUBLICATIONS

Shendure et al., "Accurate Multiplex Polony Sequencing of an Evolved Bacterial Genome", Science, Sep. 9, 2005, vol. 309, pp. 1728-1732.

Shendure et al., "Advanced Sequencing Technologies: Methods and Goals", Nature Reviews Genetics, May 2004, vol. 5, pp. 335-344.

Shendure et al., "Overview of DNA Sequencing Strategies", Current Protocols in Molecular Biology, Jan. 2008, pp. 7.1.1-7.1.11.

Shi et al., "Rapid Spine Delivery and Redistribution of AMPA Receptors After Synaptic NMDA Receptor Activation", Science, Jun. 11, 1999, vol. 284, pp. 1811-1816.

So et al., "Self-illuminating quantum dot conjugates for in vivo imaging", Nature Biotechnology, Mar. 2006, vol. 24, No. 3, pp. 339-343.

Suhling et al., "Time-resolved fluorescence microscopy", Photochem, Photobiol. Sci., 2005, vol. 4, pp. 13-22.

Sun, "Higher Harmonic Generation Microscopy", Adv Biochem Engin/Biotechnol, 2005, vol. 95, pp. 17-56.

Toth et al., "Reconstruction of a Three-Dimensional Microscopic Sample Using Holographic Techniques", Applied Physics Letters, Jul. 1, 1968, vol. 13 No. 1, p. 7-9.

Trifonov et al., "Ultrafast Energy Transfer and Structural Dynamics in DNA", J. Phys. Chem, 2005, vol. 109, pp. 19490-19495.

Truong et al., "The use of FRET imaging microscopy to detect protein-protein interactions and protein conformational changes in vivo", pp. 573-575.

Truong et al., "The use of FRET imaging microscopy to detect protein-protein interactions and protein conformational changes in vivo", Current Opinion in Structural Biology, 2001, vol. 11, pp. 573-578.

Tsien, "Fluorescent Probes of Cell Signaling", Ann. Rev. Neurosci, 1989, vol. 2, pp. 227-253.

Venter et al., "The Sequence of the Human Genome", Science, Feb. 16, 2001, vol. 291, pp. 1304-1351.

Vogt et al., "Optical Second Harmonic Generation in Sodium Nitrite", phys. stat. sol. (a), 1970, vol. 1, pp. 439-450.

Wallrabe et al., "Imaging protein molecules using FRET and FLIM microscopy", Current Opinion in Biotechnology, 2006, vol. 16, pp. 19-27.

Wang et al., "Non-blinking semiconductor nanocrystals", Nature, Jun. 4, 2009, vol. 459, pp. 686-689.

Whitesides, "The 'right' size in nanobiotechnology", Nature Biotechnology, Oct. 2003, vol. 21, No. 10, pp. 1161-1165.

Williams et al., "Fast Events in Protein Folding: Helix Melting and Formation in a Small Peptide", Biochemistry, 1996,, vol. 35, pp. 691-697.

Xu et al., "Tracking particles in four dimensions with in-line holographic microscopy", Optics Letters, Feb. 1, 2003, vol. 28, No. 3, pp. 164-166.

Yamaguchi et al., "Phase-shifting digital holography", Optics Letters, Aug. 15, 1997, vol. 22, No. 16, pp. 1268-1270.

Zal et al., "Using live FRET imaging to reveal early protein-protein interactions during T cell activation", Current Opinion in Immunology, 2004, vol. 16, pp. 418-427.

Zayats et al., "Second-harmonic generation from individual surface defects under local excitation", Physical Review B, Feb. 15, 2000, vol. 61, No. 7, pp. 4545-4548.

Zhang et al., "Three-dimensional microscopy with phase-shifting digital holography", Optics Letters, Aug. 1, 1998, vol. 23, No. 15, pp. 1221-1223.

Zhao et al., "Electrical signals control wound healing through phosphatidylinositol-3-OH kinase-_ and PTEN", Nature, Jul. 27, 2006, vol. 442, pp. 457-460.

Zipfel et al., "Nonlinear magic: multiphoton microscopy in the biosciences", Nature Biotechnology, Nov. 2003, vol. 21, No. 11, pp. 1369-1377.

FUNCTIONALIZATION OF AND USE OF FUNCTIONALIZED SECOND HARMONIC GENERATING NANOPROBES

CROSS-REFERENCE TO RELATED APPLICATIONS

The current application is a divisional application of U.S. application Ser. No. 13/683,975, filed Nov. 21, 2012, which application claimed priority to U.S. Provisional Application No. 61/562,289, filed Nov. 21, 2011, the disclosure of which is incorporated herein by reference.

STATEMENT OF FEDERAL RIGHTS

This invention was made with government support under Grant No. HD043897 and under Grant No. HG004071 awarded by the National Institutes of Health. The government has certain rights in the invention.

FIELD OF THE INVENTION

The current invention is directed to functionalized SHG nanoprobes, and methods for functionalizing and targeting SHG nanoprobes.

BACKGROUND OF THE INVENTION

One of the grand open challenges in modern science is to identify cells or probe molecules and understand the mechanism and dynamics of biological processes at the molecular level with high spatiotemporal resolution, and particularly inside living cells and tissue. As a result of the wealth of information potentially accessible from such biological targets, there has been a growing demand for imaging tools for biomedical research and medicine. This research has led to the development of new techniques like magnetic resonance imaging (MRI), ultrasound, positron emission tomography (PET), and optical coherence tomography (OCT). However, these techniques require high costs and some fundamental technological barriers hinder their widespread use.

Optical imaging is a practice that has recently gained widespread clinically relevant use that utilizes photons as an information source to analyze cells and tissues at multiple length and time scales, with applications in a wide range of basic science and clinical studies like pharmacology, cellular biology, and diagnostics. For example, semiconductor nanocrystals, small organic dyes or fluorescent proteins are commonly used as optical labels in in vivo optical imaging. (See, e.g., X. Michalet et al., Science 307, 538 (Jan. 28, 2005); B. Dubertret et al., Science 298, 1759 (Nov. 29, 2002); M. K. So, C. Xu, A. M. Loening, S. S. Gambhir, J. Rao, Nat Biotechnol 24, 339 (March, 2006); N. C. Shaner, P. A. Steinbach, R. Y. Tsien, Nat Methods 2, 905 (December, 2005); and B. N. Giepmans, S. R. Adams, M. H. Ellisman, R. Y. Tsien, Science 312, 217 (Apr. 14, 2006), the disclosures of which are incorporated herein by reference.) Indeed, recent advances in fluorescence microscopy alone have profoundly changed how cell and molecular biology is studied in almost every aspect. (For example, see, Lichtman, J. W. & Conchello, J. A. Nat. Methods 2, 910-919 (2005); Michalet, X. et al. Annu. Rev. Biophys. Biomolec. Struct. 32, 161-182 (2003); Jares-Erijman, E. A. & Jovin, T. M. Nat. Biotechnol. 21, 1387-1395 (2003); Bastiaens, P. I. H. & Squire, A., Trends Cell Biol. 9, 48-52 (1999); and Suhling, K., et al, Photochem. Photobiol. Sci. 4, 13-22 (2005), the disclosures of which are incorporated herein by reference.)

However, the ultimate need of characterizing biological targets is largely unmet due to fundamental deficiencies associated with the use of fluorescent agents. For example, fluorescent probes face two major limitations that have a significant impact on the signal strength: 1) dye saturation, because the number of photons emitted by the fluorophore in a given time is restricted by the excited state lifetime, and 2) dye bleaching, which limits the total number of photons produced per dye. In addition, autofluorescence from tissue organic components after illumination absorption can severely limit the signal-to-noise ratio of fluorescence imaging experiments. Finally, fluorescence is fundamentally an optically incoherent process, and as a result extracting 3D information from the source is inherently difficult.

To overcome these limitations, a new kind of second harmonic generating (SHG) imaging nanoprobe has been developed. These SHG nanoprobes are characterized by photophysical properties that are fundamentally different to conventional probes, such as fluorescent agents. In particular the nonlinear nanocrystal SHG nanoprobes such as barium titanate ($BaTiO_3$) provide a unique combination of advantageous properties inherent to the SHG process that allow experiments characterizing molecular targets with excellent sensitivity for an indefinite length, with fast acquisition rates and superb signal-to-noise ratio (SNR). Accordingly, it has been recognized that SHG nanoprobes offer great potential to give insights into the dynamics of various biological targets at the molecular level with unmatched sensitivity and temporal resolution for both molecular imaging and clinical diagnostics. (See, e.g., U.S. Pat. Pub. Nos. 2012-0141981 and 2010-0233820, the disclosures of which are incorporated herein by reference.)

However, because inherent material properties targeting mechanism do not provide the targeting or delivery characteristics desired, methods to modify SHG nanoprobes with relevant chemical and biological agents are needed. Accordingly, a need exists for functionalized and targeted SHG nanoprobes, and methods of functionalizing and targeting these nanoprobes.

SUMMARY OF THE INVENTION

The current invention is directed to functionalized nanoprobes for imaging/detecting structures and biological processes based on a novel second harmonic (SH) technique, and methods for functionalizing such nanoprobes. In some embodiments, the invention is directed to a method of functionalizing second harmonic generating probe nanostructure including:

providing a probe nanostructure formed from a nanocrystalline material capable of exposing free surface hydroxyls, the probe nanostructure defining an outer surface and having no inversion symmetry such that it generates a second harmonic emission when radiated by an external excitation source;

hydroxylating the probe nanostructure to form an activated outer surface thereof;

attaching a plurality of modifying molecules having amine terminal groups to the hydroxylates of the activated outer surface of the probe nanostructure to form a functionalization platform on the outer surface of the probe nanostructure; and functionalizing the amine terminal groups of the functionalization platform with a plurality of functionalization molecules to form a functionalized probe nanostructure.

In one embodiment, the nanocrystalline material is selected from $BaTiO_3$, SiC, ZnO, $LiNbO_3$, $KNbO_3$, KTiOPO$_4$, Fe(IO$_3$)$_3$, N-(4-nitrophenyl)-(L)-prolinol, urea, 4-Nitroaniline, 2-Methyl-4-nitroaniline, 3-Methyl-4-methoxy-4'-nitrostilbene), β-BaB$_2$O$_4$, LiB$_3$O$_5$, KH$_2$PO$_4$, NH$_4$H$_2$PO$_4$, KD$_2$PO$_4$, CsLiB$_6$O$_{10}$, KTiOAsO$_4$, LiTaO$_3$, RbTiOAsO$_4$, BiB$_3$O$_6$, K$_2$Al$_2$B$_2$O$_7$, KBe$_2$BO$_3$F$_2$, BaAlBO$_3$F$_2$, La$_2$CaB$_{10}$O$_{19}$, GdCa$_4$O(BO$_3$)$_3$, YCa$_4$O(BO$_3$)$_3$, Li$_2$B$_4$O$_7$, LiRbB$_4$O$_7$, RbTiOPO$_4$, KB$_5$O$_8$.4H$_2$O, CsB$_3$O$_5$, C$_4$H$_7$D$_{12}$N$_4$PO$_7$, a-HIO$_3$, LiCOOH.H2O, CsH$_2$AsO4, CsD$_2$AsO$_4$, RbH$_2$PO$_4$, CsTiOAsO$_4$, Ba$_2$NaNb$_5$O$_{15}$, K$_3$Li$_2$Nb$_5$O$_{15}$, CO(NH$_2$)$_2$, and LiIO$_3$.

In another embodiment, the functionalization platform is formed using an amine functionalized reagent selected from N-aminoethyl-2,2,4-trimethyl-1-aza-2-silacyclopentane, 3-aminopropyltriethoxysilane, and 3-aminopropyltrimethoxysilane, N-succinimidyl S-acetylthioacetate, isothiocyanates, acyl azides, N-hydroxysuccinimide esters, sulfonyl chloride derivatives, epoxides, fluorobenzene derivatives, and carbonate compounds.

In still another embodiment, the functionalization of the functionalization platform includes a method selected from PEGylation, biocompatible polymers, click chemistry, antibody, other cell or protein selective targeting, and molecular targeting. In one such embodiment, the PEGylation is one of either monofunctionalized or multifunctionalized. In another such embodiment, the PEGylation is mono functionalized and forms a non-bio-reactive coating on the probe nanostructure. In still another such embodiment, the PEGylation is multifunctionalized and increases the bio-reactivity of the probe nanostructure through a PEG analogue selected from biotin, bromo, amino, aminoethyl, carboxymethyl, succinimidosuccinate, tosylate, mesylate, aldehyde, actadecylamine, monopalmitate, and stearoyloxy derivatives of PEG. In yet another such embodiment, the biocompatible polymer is polyacrylic acid. In still yet another such embodiment, the click chemistry is one of either a copper free or copper catalyzed chemistry. In still yet another such embodiment, the antibody is a glycosylated antibody originating from a host of interest.

In yet another embodiment, the functionalization molecule is designed to one of either target or label a specific cell or molecule of interest.

In still yet another embodiment, the functionalization molecule renders the probe nanostructure acceptable for use in conjunction with a technique selected from SHG imaging, direct nucleic acid sequencing in a Multi-SHG Detection Imaging modality, FRESH, optical monitoring of electric fields, imaging/detecting medical conditions or neoplasm, detection or tracking of therapeutic agents, and rapid detection systems.

In still yet another embodiment, the functionalized probe nanostructure includes a plurality of different functionalization molecules.

In still yet another embodiment, the functionalized probe nanostructure includes a single species of functionalization molecule.

In still yet another embodiment, the functionalized probe nanostructure further includes at least one linkage between the functionalization platform and the functionalization molecule.

In other embodiments, the invention is directed to a functionalized probe nanostructure including:
  a nanocrystalline body capable of exposing free surface hydroxyls defining an outer surface and having no inversion symmetry such that it generates a second harmonic signal when illuminated by an external excitation source,
  a functionalization platform comprising a plurality of modifying molecules having amine terminal groups, the modifying molecules being linked to the outer surface of the body through a plurality of hydroxyl molecules; and
  a plurality of functionalization molecules bound to the amine terminal groups of the functionalization platform.

In one embodiment, the nanocrystalline body is selected from BaTiO$_3$, SiC, ZnO, LiNbO$_3$, KNbO$_3$, KTiOPO$_4$, Fe(IO$_3$)$_3$, N-(4-nitrophenyl)-(L)-prolinol, urea, 4-Nitroaniline, 2-Methyl-4-nitroaniline, 3-Methyl-4-methoxy-4'-nitrostilbene), β-BaB$_2$O$_4$, LiB$_3$O$_5$, KH$_2$PO$_4$, NH$_4$H$_2$PO$_4$, KD$_2$PO$_4$, CsLiB$_6$O$_{10}$, KTiOAsO$_4$, LiTaO$_3$, RbTiOAsO$_4$, BiB$_3$O$_6$, K$_2$Al$_2$B$_2$O$_7$, KBe$_2$BO$_3$F$_2$, BaAlBO$_3$F$_2$, La$_2$CaB$_{10}$O$_{19}$, GdCa$_4$O(BO$_3$)$_3$, YCa$_4$O(BO$_3$)$_3$, Li$_2$B$_4$O$_7$, LiRbB$_4$O$_7$, RbTiOPO$_4$, KB$_5$O$_8$.4H$_2$O, CsB$_3$O$_5$, C$_4$H$_7$D$_{12}$N$_4$PO$_7$, a-HIO$_3$, LiCOOH.H$_2$O, CsH$_2$AsO4, CsD$_2$AsO$_4$, RbH$_2$PO$_4$, CsTiOAsO$_4$, Ba$_2$NaNb$_5$O$_{15}$, K$_3$Li$_2$Nb$_5$O$_{15}$, CO(NH$_2$)$_2$, and LiIO$_3$.

In another embodiment, the functionalization platform is formed from an amine functionalized reagent selected from N-aminoethyl-2,2,4-trimethyl-1-aza-2-silacyclopentane, 3-aminopropyltriethoxysilane, and 3-aminopropyltrimethoxysilane, N-succinimidyl S-acetylthioacetate, isothiocyanates, acyl azides, N-hydroxysuccinimide esters, sulfonyl chloride derivatives, epoxides, fluorobenzene derivatives, and carbonate compounds.

In still another embodiment, the functionalization molecules are bound to the functionalization platform through a linkage selected from mono functional or multifunctional PEGylation, biocompatible polymers, click chemistry, antibody targeting, other cell or protein-selective targeting, and other molecule targeting.

In yet another embodiment, the functionalization molecule is selected from the group of a non-bio-reactive coating and a bio-reactivity enhancer.

In still yet another embodiment, the bio-reactivity enhancer is a PEG analogue selected from biotin, bromo, amino, aminoethyl, carboxymethyl, succinimidosuccinate, tosylate, mesylate, aldehyde, actadecylamine, monopalmitate, and stearoyloxy derivatives of PEG.

In still yet another embodiment, the functionalization molecule is a glycosylated antibody originating from a host of interest.

In still yet another embodiment, the functionalization molecule is configured to target or label a specific cell, biological molecule or molecule of interest.

In still yet another embodiment, the functionalized probe nanostructure is configured to be acceptable for use in conjunction with a technique selected from SHG imaging, direct nucleic acid sequencing in a Multi-SHG Detection Imaging modality, FRESH, optical monitoring of electric fields, imaging/detecting medical conditions or neoplasm, detection or tracking of therapeutic agents, and rapid detection systems.

In still yet another embodiment, the functionalized probe nanostructure includes a plurality of different biologically relevant functionalization molecules.

In still yet another embodiment, the functionalized probe nanostructure further includes at least one additional linkage between the functionalization platform and the biologically relevant functionalization molecule.

In still other embodiments, the invention is directed to method of probing structures and biological processes including:
  interspersing a functionalized probe nanostructure configured with a biologically relevant functionalization molecule bound to the probe nanostructure through a functionalization platform including a plurality of modifying molecules having amine terminal groups, the modifying molecules being linked to the outer surface of the body through a plurality of hydroxyl molecules, and wherein the probe nanostructure has no inversion symmetry such that it generates a second harmonic signal when illuminated by an excitation source;

the functionalization molecule being selected to target a species of interest, such that the functionalized probe nanostructure interacts with the targeted species of interest;

illuminating the probe nanostructure with an external excitation source; and detecting the second harmonic signal from the nanoprobe.

In one embodiment, the targeted species of interest is selected from antigen, a peptide sequence, a nucleic acid sequence, RNA, DNA, and a sugar/carbohydrate group.

In another embodiment, wherein the targeted species of interest is indicative of the presence of one of either a specific medical condition or a specific pathogenesis.

In still another embodiment, the functionalized probe nanostructure is directly attached to the targeted species of interest through the functionalization molecule.

In yet another embodiment, the probe nanostructure is conjugated through the functionalization molecule to a probe molecule that is sensitive to the presence of the targeted species of interest.

In still yet another embodiment, the step of illuminating is conducted while the probe nanostructure is external to the source of the targeted species of interest.

In still yet another embodiment, the step of illuminating is conducted while the probe nanostructure is in vivo to the source of the targeted species of interest. In one such embodiment, the signal from the probe nanostructure is utilized to image the specific location of the targeted species of interest within the source of the target of interest.

In still yet another embodiment, the method further comprises incorporating an exciter nanostructure to the targeted species of interest, said exciter nanostructure designed to produce a resonant electrical field of a specified frequency when exposed to an excitation source, wherein the functionalized probe nanostructure generates a second harmonic resonance emission when brought within range of the resonant electrical field of said exciter nanostructure.

In still yet another embodiment, the excitation source is selected from a two-photon source, a nanosecond pulsed laser, a picoseconds pulsed laser, a femtosecond pulsed laser, and an attosecond pulsed laser.

BRIEF DESCRIPTION OF THE DRAWINGS

The description and claims of the current invention will be more fully understood with reference to the following figures and data graphs, which are presented as exemplary embodiments of the invention and should not be construed as a complete recitation of the scope of the invention, wherein:

FIG. 14a (a) shows the sugar residues on the Fc region of the antibody are oxidized with sodium periodate, and where.

DETAILED DESCRIPTION OF THE INVENTION

Functionalized and targeted SHG nanoprobes, methods for functionalizing and selectively targeted nanoprobes capable of producing second harmonic generation are presented in the figures and description. The embodiments presented provide methods and strategies to functionalize and target SHG nanoprobes including the surface modification of these entities with synthetic polymers (to afford long-circulating properties), targeting ligands for selective attachment at desired sites, and to attaching antibodies.

By designing a broadly applicable surface functionalization methodology, these SHG nanoprobes can be rendered more relevant to a wide-variety of imaging applications. For example, SHG nanoprobe functionalization and targeting will allow the implementation of, among other things:

general SHG imaging for basic science research,
direct nucleic acid sequencing in a Multi-SHG Detection Imaging modality (MSDI),
the field resonance enhanced second harmonic (FRESH) technique,
optical monitoring of electric fields,
imaging/detecting medical conditions or neoplasm,
detection or tracking of therapeutic agents, and
rapid detection systems to be used by primary care level practitioners and field workers in hospitals or doctor's offices.

Moreover, the SHG nanoprobe functionalization and targeting described in the embodiments provided is straightforward and robust, allowing multiple varieties as well as serial/parallel linkage modifications (in this instance, serial means step-wise functionalization, and parallel means simultaneous functionalization).

SHG Nanoprobe Overview

Figure 1:
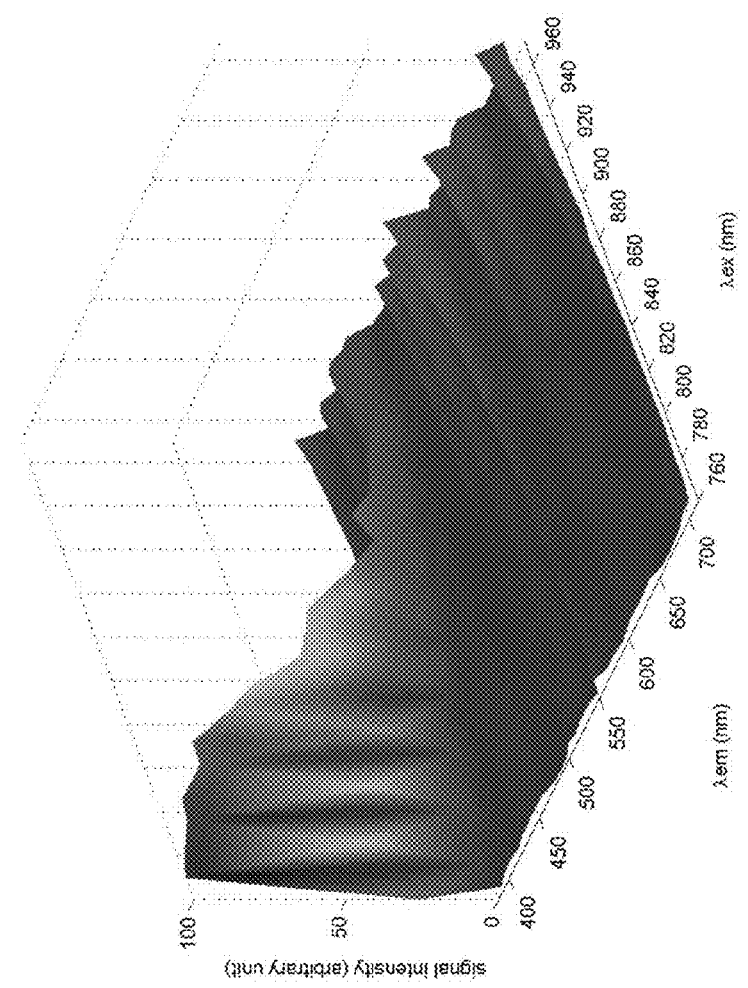
FIG. 1 provides a detected signal profile of an exemplary second harmonic generation nanocrystal probe in accordance with the current invention (Prior Art).

Previous studies have shown that second harmonic generating (SHG) nanoprobes are suitable for (in vivo) imaging/detecting and can avoid most of the inherent drawbacks encountered in classical optical systems. (See, e.g., U.S. Pat. Pub. Nos. 2012-0141981 and 2010-0233820, cited above.) SHG nanoprobes are nonlinear materials, e.g., various kinds of inorganic and/or organic nanocrystals that do not possess an inversion symmetry and therefore are capable of generating second harmonic signals. Such structures may be any organic, inorganic or combination of organic and inorganic nanocrystal, such as, for example BaTiO3, SiC, ZnO, LiNbO3, urea or N-(4-nitrophenyl)-(L)-prolinol (NPP). Typical SH signal might range for example from 350 to 700 nm, although other wavelengths might be used dependent on the material to be imaged (see, the exemplary SH signal profile shown in FIG. 1). The SH signal can then be detected by any optical based technique, such as for example, conventional two-photon microscopy (for example, for wavelengths in the range of 350 to 700 nm by tuning the wavelength from 700 to 1400 nm), or other pulsed lasers having for example nano, pico or femtosecond timeframes.

Although a few specific examples of possible probe nanostructure nanocrystals are described above, it should be understood that any nanostructure, defined hereinafter as a structure of ≤1 μm, capable of second harmonic generation may be used in the current invention. The one significant limitation on the materials, as discussed above, being that for second harmonic generation it is required that the crystal structure of the nanostructure not possess an inversion symmetry center.

Figure 2:
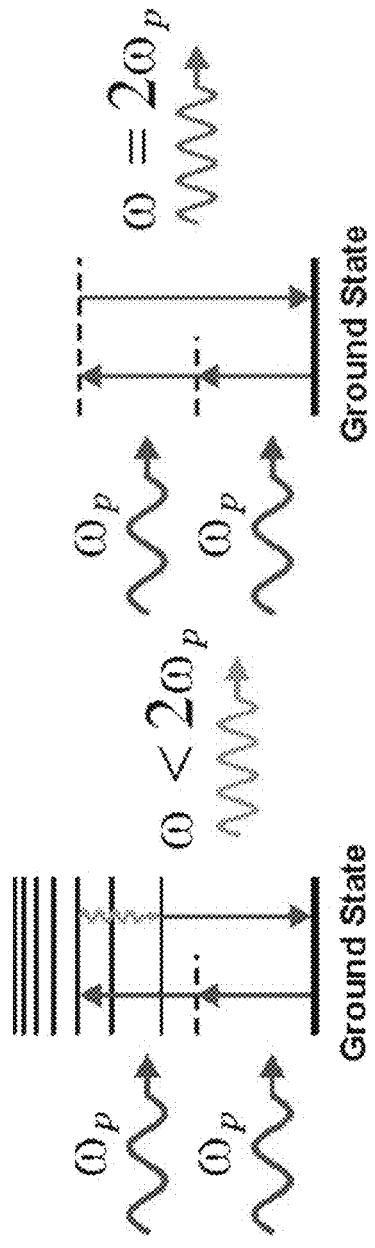
FIG. 2 provides a schematic diagram comparing the properties of the imaging technique of the current invention with conventional optical systems (Prior Art).

Second harmonic generation has many inherent advantages over fluorescence that open the possibility of a wide variety of applications. These advantages are discussed with reference to the schematic diagram provided in FIGS. 2 to 4, which are taken from U.S. Patent Pub. No. 2012-0141981.

First, as a parametric nonlinear optical process, second harmonic generation does not involve real electron energy transition but only virtual transitions. Fluorescence, on the other hand, involves actual energy transition of electrons. As a result, the response time of second harmonic generation is at the femtosecond level, about four to five orders of magnitude faster than the nanosecond response time of fluorescence, allowing very fast and sensitive detection of molecules with appropriate detection systems. (See, e.g., R. W. Boyd, *Nonlinear optics* (Academic Press, San Diego, Calif., ed. 2nd, 2003), pp. xvii, 578 p, the disclosure of which is incorporated herein by reference.)

Second, biological tissue does not often assemble into large, ordered noncentrosymmetric structures. As a result, biological tissue does not generate a strong SH signal, therefore, the second harmonic generating crystals can be imaged with sharp contrast (high signal-to-noise ratio) when present in vivo, allowing detection of single molecules or identification of cells of interest in tissue.

Figure 3:
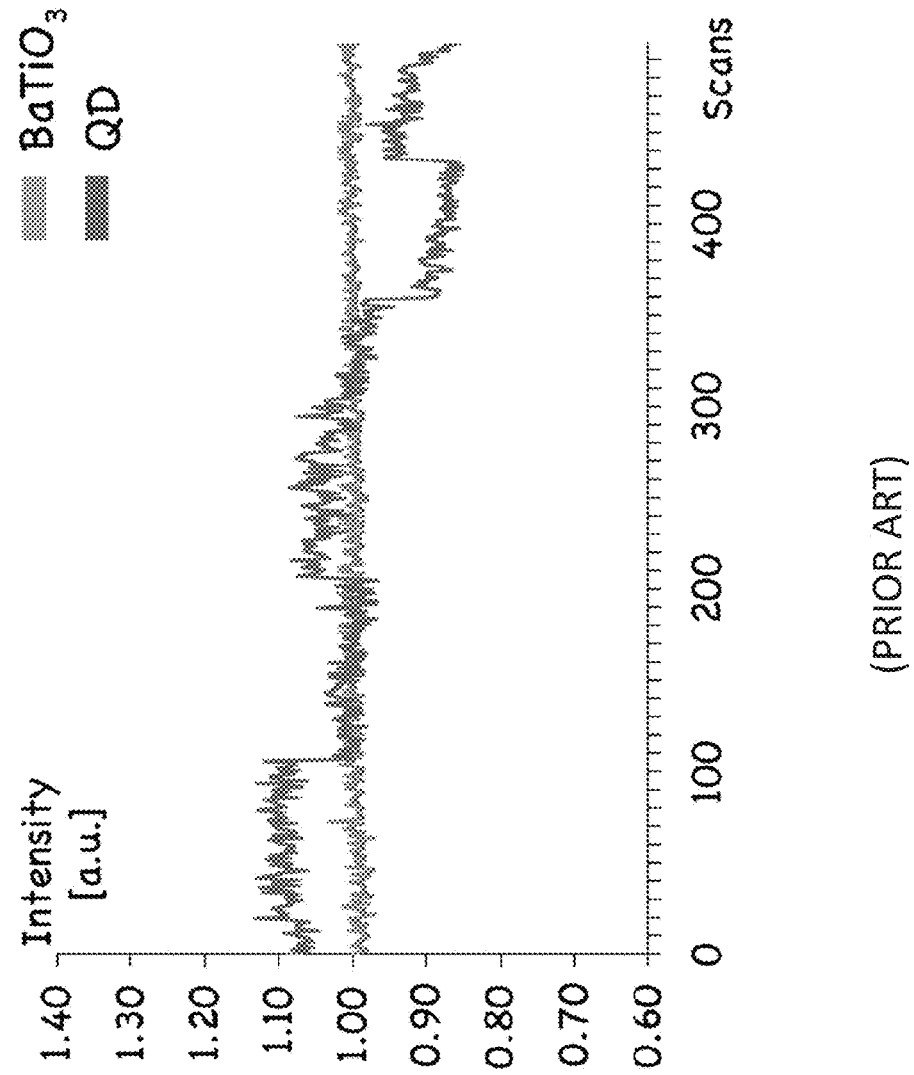
FIG. 3 provides a set of data graphs showing the comparative bleaching and blinking properties for an exemplary second harmonic generation nanocrystal probe in accordance with the current invention and a conventional quantum dot (Prior Art).

Third, unlike fluorescent dyes, second harmonic generating nanocrystals do not undergo photo-bleaching or blinking, as shown in FIG. 3. In this set of data graphs, SHG single BaTiO₃ nanocrystals and CdSe/ZnS quantum dots (QD) were immobilized in 20% polyacrylamide and illuminated 500 times within 25 s with 820 nm light. As shown, whereas the second harmonic signal intensity of BaTiO₃ is constant, the QD signal fluctuates, displaying sub-blinking as well as major blinking and photobleaching events, making it a superior single molecule detection probe. (See, e.g., W. Denk, J. H. Strickler, W. W. Webb, *Science* 248, 73 (Apr. 6, 1990), the disclosure of which is incorporated herein by reference.)

Figure 4:
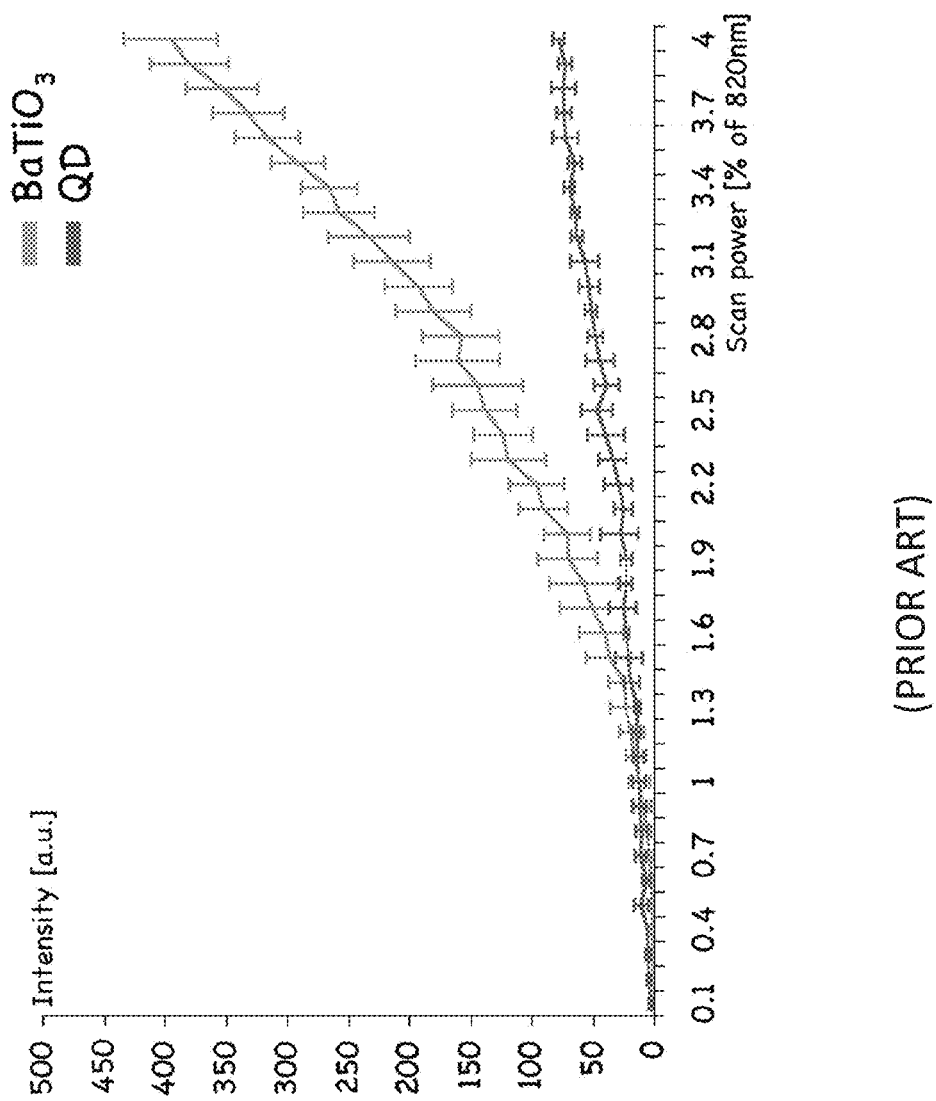
FIG. 4 provides a set of data graphs showing the saturation properties for an exemplary second harmonic generation nanocrystal probe in accordance with the current invention and a conventional quantum dot (Prior Art).

Fourth, again unlike fluorescent dyes, SHG nanocrystals do not undergo photo-saturation with increasing illumination intensity, as shown in FIG. 4. In this set of data graphs, BaTiO₃ nanocrystals and CdSe/ZnS quantum dots (QD) were immobilized in 20% polyacrylamide and illuminated with increasing 820 nm light intensity. As shown, signal saturation of QD occurs already at very low power levels, whereas the second harmonic signal of BaTiO₃ nanocrystals increases quadratically, allowing very efficient visualization or detection of, for example, a single molecule attached to such a nanoprobe crystal, for example, in tissue or sample solution by simply increasing the illumination power. (See, e.g., C. K. Sun, *Adv Biochem Eng Biotechnol* 95, 17 (2005), the disclosure of which is incorporated herein by reference.)

Finally, the SHG nanocrystal probes of the current invention show a high pH stability allowing targeting a wider range of molecules of interest, such as, for example, acidic organelles without signal loss.

Functionalization/Targeting of SHG Nanoprobes

The basic principle behind the operation of SHG nanoprobes is to attach to a molecule of interest a probe nanostructure that generates a second harmonic signal or to identify cells or tissue of a living subject (in vivo) using such probe nanostructures. However, because inherent material properties do not provide the targeting or delivery characteristics desired, methods of functionalizing and targeting SHG nanoprobes would greatly enhance the usefulness of the probes.

Applications for functionalized SHG nanoprobes in biology are wide ranging. Potentially, the most important feature of these nanocrystals is that they offer a compatible spectral signature to any fluorescent protein or dye currently used in biological imaging—unlike the absorption band that is an inherent property of fluorescent probes, the anti-Stokes shift that is characteristic of SHG signal can be tuned for any application. (See, Pantazis, P., Maloney, et al., Proc. Natl. Acad. Sci. USA 107, 14535-14540 (2010), the disclosure of which is incorporated herein by reference.) Generally, by choosing a proper 2P illumination wavelength and proper emission filter sets, both SHG signal and fluorescent emission can be simultaneously collected and spectrally separated. In addition, given the distinct wavelength dependence of SHG signal in different SHG nanoprobes, multiple varieties of SHG nanoprobes may be combined to achieve a spectrally separable signal. Thus, functionalized SHG nanoprobes may be used in conjunction with traditional fluorescent labels as an additional unique spectral label for multimarker imaging, such as is necessary for long term stem cell tracking at the level of a single cell in culture and in vivo. (See, e.g., Staedler, D. et al., ACS Nano 6, 2542-2549 (2012) and Schroeder, T., Nat. Methods 8, S30-S35 (2011), the disclosure of which is incorporated herein by reference.)

Other applications include the use of a bolus of dispersed SHG nanoprobes as indelible markers for lineage-tracing experiments within living organisms, as these probes should redistribute within some number of subsequent daughter cells after successive divisions during development or regeneration, replacing or acting in conjunction with traditional dye-injection or cell transplantation strategies. (See, Cohen, B. E., Nature 467, 407-408 (2010) and Buckingham, M. E. & Meilhac, S. M., Dev. Cell 21, 394-409 (2011), the disclosures of which are incorporated herein by reference.) The benefit of the SHG nanoprobes is that they may be especially attractive for applications in higher-order vertebrates, as their bright, high signal-to-noise ratio will be of particular interest, as these embryos become more absorptive and scattering as development proceeds past the gastrula period. (Grange, R., et al., Biomed. Opt. Express 2, 2532-2539 (2011), the disclosure of which is incorporated herein by reference.)

A streptavidin conjugation after biotinylation of the surface of, for example, $BaTiO_3$ would allow for selective attachment to biotinylated molecules for specific cell targeting—such as receptor ligands or antibodies—as was described previously for quantum dots. (See, Jaiswal, J. K., et al., Nat. Methods 1, 73-78 (2004), the disclosure of which is incorporated herein by reference.) The protocol can also be extended to directly conjugate antibodies to the surface through covalent means atop the proposed amine-terminal platform surface functionalization, which would also enable specific cell labeling for immunostaining, as well as live cell targeting. (See, Hsieh, C. L., et al., Biomaterials 31, 2272-2277 (2010), the disclosure of which is incorporated herein by reference.)

In addition to allowing for more effective biological imaging and targeting, another consideration in favor of functionalization is that most of these nanoprobe materials are commercially derived and are heterogeneous in size. This heterogeneity is twofold: (1) the process of production of these nanomaterials through the commercial source often results in a broad distribution of nanoparticle sizes, ranging from 50-200 nm; and (2) the nanoparticles are sold in dry powder form, leading to significant aggregation of the particles. Proper functionalization could at least limit the two size heterogeneity issues by creating a barrier around each individual nanoparticle (or smaller cluster that cannot be broken apart from sonication), preventing further aggregation.

This size issue is of particular relevance for targeting in an in vivo system, where efficient uptake and diffusion into tissue extracellular spaces (e.g., with gold nanoparticles) as well as eventual clearance from the body (e.g., with quantum dots) has been shown to be strongly dependent on the size of the nanoparticle itself. This, along with other considerations for designing clinically relevant nanoparticles for biological applications, led to the current functionalization scheme.

Figure 5:
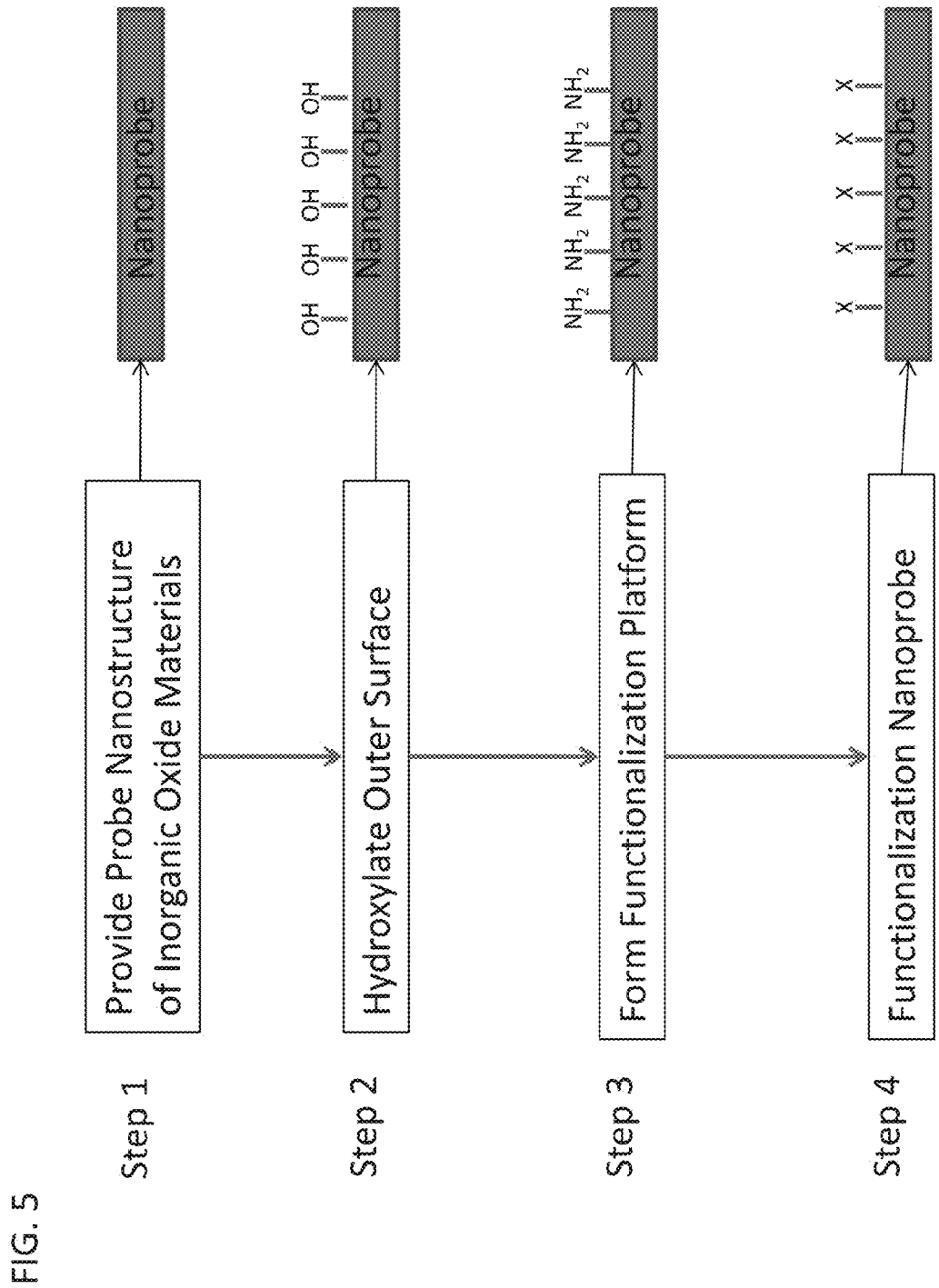
FIG. 5 provides a flow chart showing embodiments of a method for functionalizing SHG nanoprobes, in accordance with the current invention.

The flowchart shown in FIG. 5 provides an exemplary methodology for functionalizing and targeting SHG nanoprobes in accordance with certain embodiments of the invention. Although the following example uses $BaTiO_3$ as the exemplary material, it should be understood that any nanocrystalline SHG nanoprobe material capable of exposing free surface hydroxyl groups may be functionalized in accordance with the embodiments disclosed herein.

As shown, in a first step, the surface of the SHG nanoprobe is modified to activate the surface of the nanoprobe material. For example, in one embodiment the nanoprobe material is modified to expose more hydroxyl groups on the surface of the probe, which in turn makes the surface of the nanoprobe more susceptible to activation and functionalization. Although many different methods exist for activating and exposing such hydroxyl groups, in one example the method may include treating the SHG nanoprobe with hydrogen peroxide and sonication.

In a second step, the activated (e.g., hydroxylated) SHG nanoprobe is then modified to create a "surface modified platform" upon which further functionalization can be performed. Again, although many different surface modified platforms may be created that are compatible with activated inorganic oxide SHG nanoprobes, in one exemplary embodiment an amine-coated surface is formed using, for example, N-aminoethyl-2,2,4-trimethyl-1-aza-2-silacyclopentane.

This is a particular useful reaction pathway because of its ease of use and the lack of byproduct formation during functionalization reaction (thus eliminating extraneous washing steps). However, a plethora of amine-functionalized reagents exist that can be used to achieve the same effect, e.g. 3-aminopropyltriethoxysilane (APTES), 3-aminopropyltrimethoxysilane (APTMS), etc.

Figure 6A:
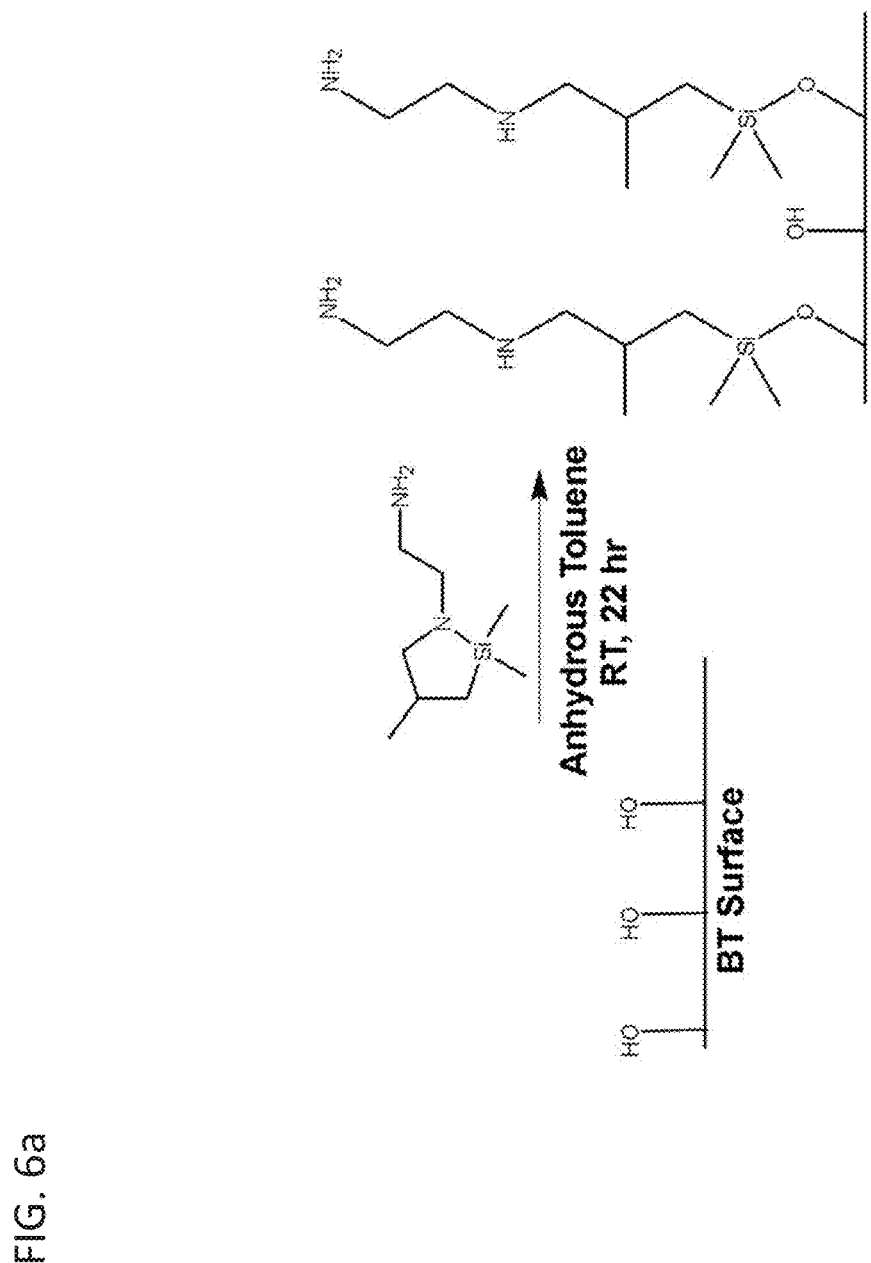
FIGS. 6a to 6d provide chemical schematics of $BaTiO_3$ surface modifications, wherein FIG. 6a shoes that after hydroxylation of the surface, $BaTiO_3$ is silanized, exposing an $NH_2$ domain that acts as a platform for further modification by: (1) PEG, as shown in FIG. 6b, (2) click chemistry, as shown in FIG. 6c, and (3) antibody linkages, as shown in FIG. 6d, which are a subset of the possible functionalization routines that are possible using the silanated surface as a platform, in accordance with the current invention.
Figure 6B:
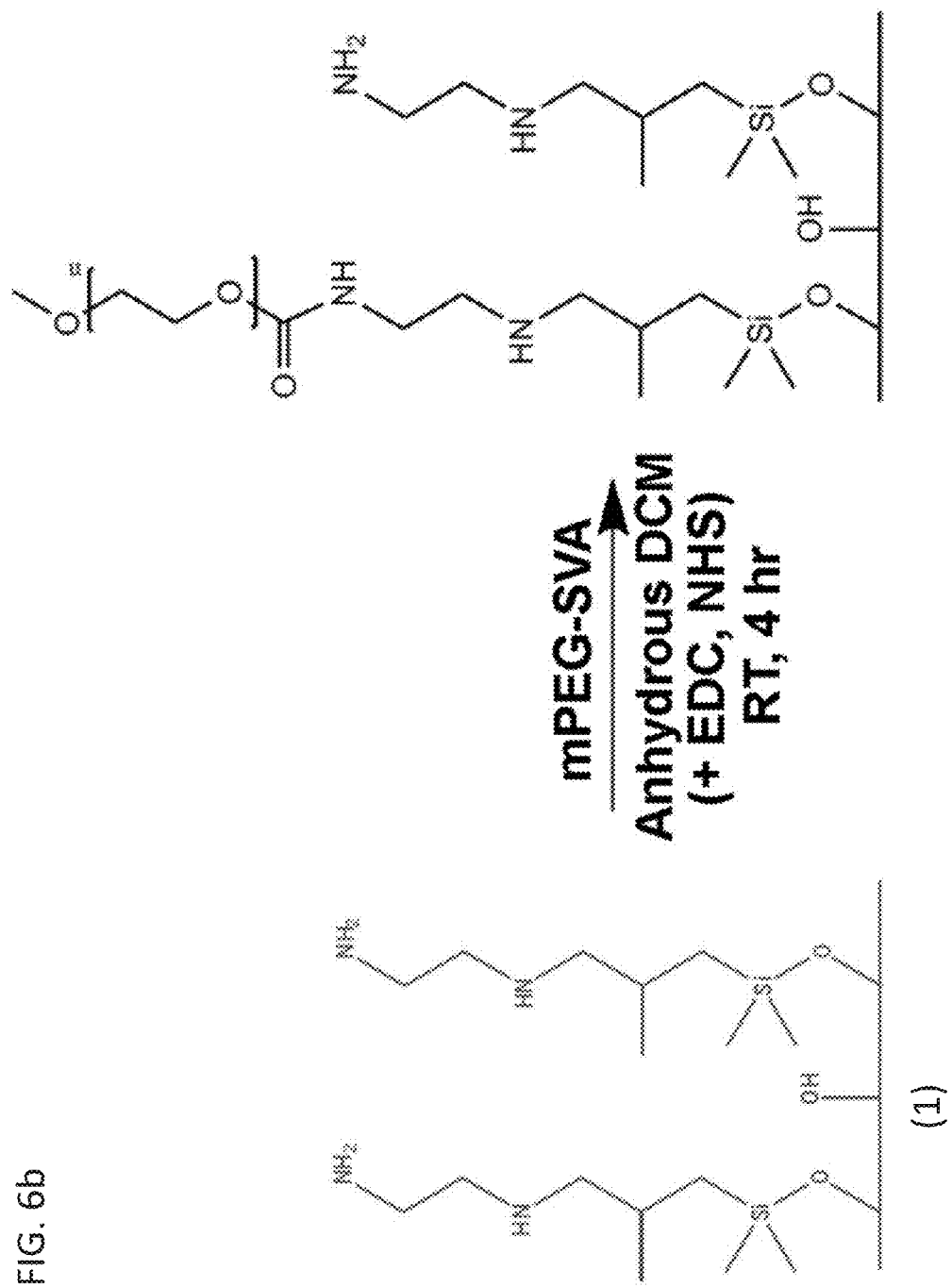

Such amine modified SHG nanoprobes create a reactive surface platform that will is susceptible to further chemical functionalization and targeting tailored for specific biological applications. Some exemplary functionalizations are shown in FIGS. 6a to 6d and include:

PEGylation:

PEGylation with monofunctionalized PEG moieties (as shown in FIG. 6b) act as a non-bio-reactive coating for the SHG nanoprobes, while multifunctionalized (e.g. bifunctional, "star"-PEG, etc.) PEG moieties allow the attachment of SHG nanoprobes to various biological targets (e.g. protein, lipids, DNA, RNA, etc.). This increased bio-reactivity may be achieved by covalent coupling with a number of simple PEG analogues, such as, for example, biotin, bromo, amino, aminoethyl, carboxymethyl, succinimidosuccinate, tosylate, mesylate, aldehyde, actadecylamine, monopalmitate, and stearoyloxy derivatives of PEG. The use of other biocompatible polymers—such as the poly(acrylic acid) polymer—can provide an even more widespread binding to the $BaTiO_3$ surface than PEG, enabling greater surface coverage.

Figure 6C:
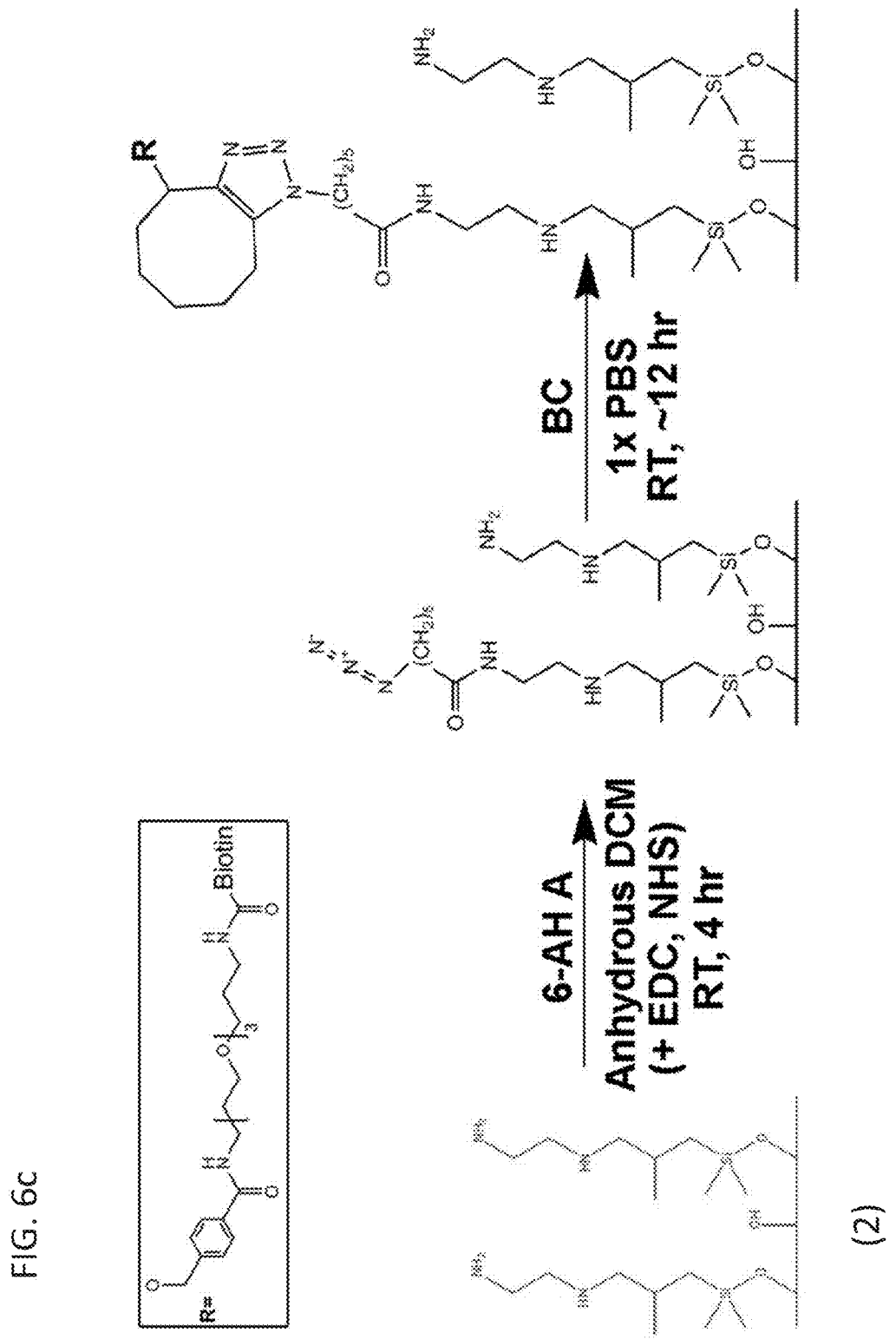

Click Chemistry:

Click chemistry tools can be used for efficient, high yield surface functionalization of the SHG nanoprobe platforms for both copper free (such as shown in FIG. 6c with the interaction of biotin-cyclooctyne and azido functionalized $BaTiO_3$), as well as copper catalyzed chemistries. It is important to note that while the high-yield click chemistry linkage used in this protocol provides a robust way to guarantee that the functionalization platform could withstand the addition of several linkage groups, alternative, commercially available reagents exist that enable direct linkage of biotin to the surface amines (such as variety of biotin-NHS linkers). In addition, an alternative click chemistry method for coating silica nanospheres with polymer brushes has been demonstrated, which may be a useful protocol to adapt for use with SHG nanoprobes. (See, Li, G. L., et al., Macromolecules 43, 10275-10282 (2010), the disclosure of which is incorporated herein by reference.) Thus, a variety of methods are possible to achieve different linkage chemistries utilizing the convenient and readily reactive amine functional groups on the surface of, for example, $BaTiO_3$—$NH_2$.

Figure 6D:
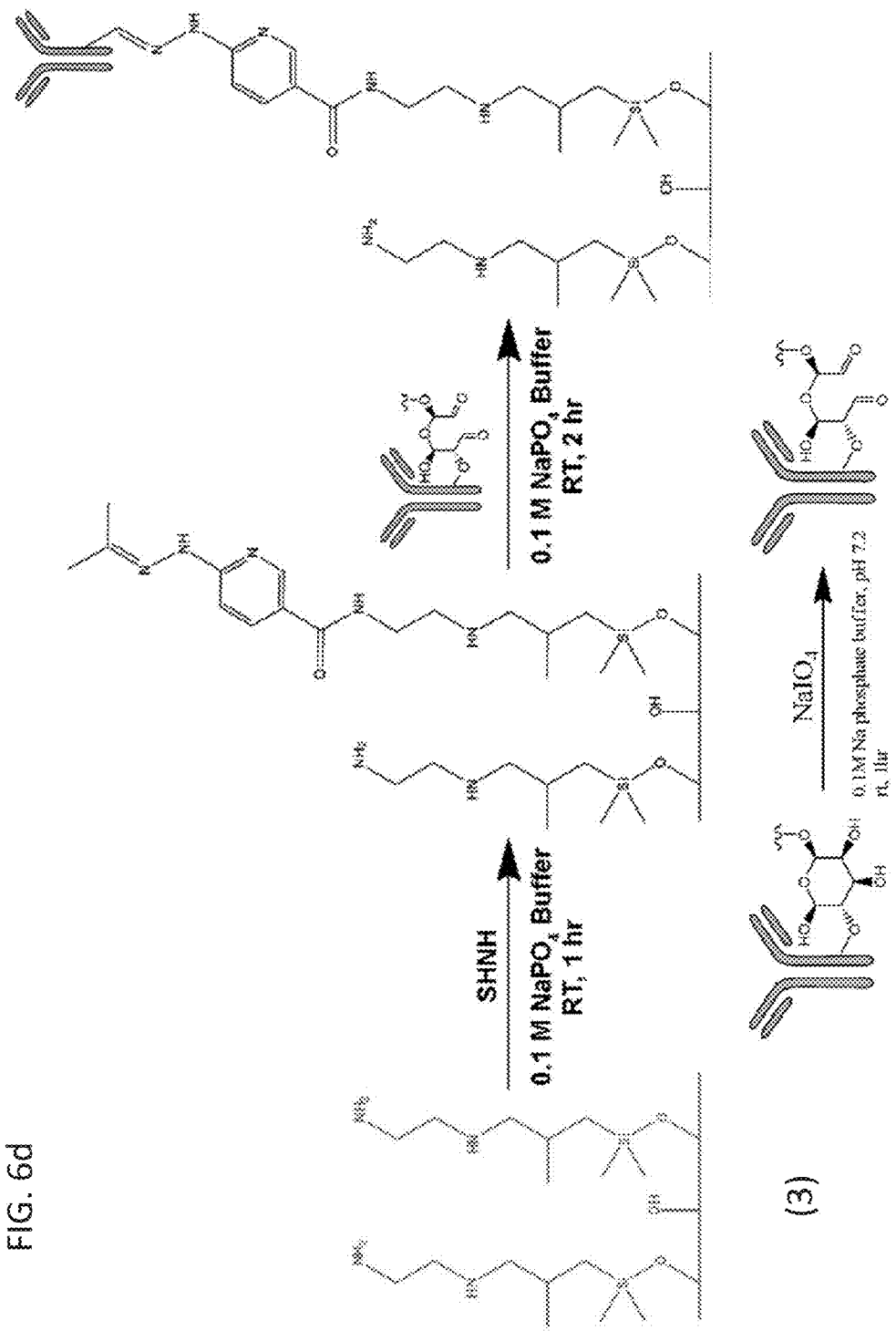

Antibody Targeting:

For specific surface targeting, any glycosylated antibody (primary or secondary originating from a mammalian host, for example) can be attached to the surface of the SHG nanoprobes (as shown in FIG. 6d). Thus, specific targeting within any model organism is solely limited by the choice of antibody used during functionalization.

Other Systems:

Note that these examples are not the only functionalization schemes with amine available. A variety of alternate functionalization routines include, but are not limited to: N-succinimidyl S-acetylthioacetate (SATA), isothiocyanates, acyl azides, N-hydroxysuccinimide esters, sulfonyl chloride derivatives, epoxides, fluorobenzene derivatives, carbonate compounds, etc.

Figure 7:
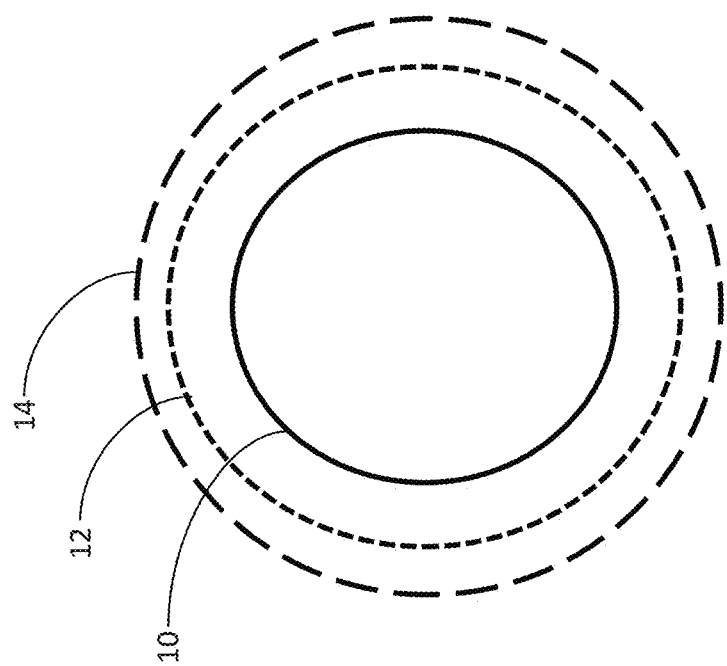
FIG. 7 provides a schematic of embodiments of a functionalized SHG nanoprobe, in accordance with the current invention.

Although the above discussion and figures focus on methods of functionalizing nanoprobes, it should be understood that embodiments are also directed to functionalized nanoprobes themselves. A schematic of the nanoprobes is shown in FIG. 7. In particular, the functionalized nanoprobes of the instant invention have three separate structures, a nanocrystalline nanoprobe core (10), having an outer surface having attached thereto a plurality of pre-functionalization molecules that in combination form a functionalization platform (12). The functionalization platform itself is formed of a plurality of hydroxylated moieties attached to the nanoprobe core, and an amine terminal group attached to the hydroxyl moieties through an appropriate linker, such as a silane group. Finally, the nanoprobe is provided with a functionalization (14) linked to the nanoprobe through the functionalization platform (12), that is targeted to a specific target. In turn, this target may be biological or non-biological in nature, as described elsewhere herein.

Finally, although many of the examples above and in the following sections describe the use of $BaTiO_3$ specifically, it should be understood that the nanoprobes may be made from any nanocrystalline material capable of exposing hydroxyl groups on their surface. Candidate SHG nanoprobes with this property are, for example, inorganic oxides with high second-order susceptibility, such as, for example, $BaTiO_3$, SiC, ZnO, $LiNbO_3$, $KNbO_3$, $KTiOPO_4$, $Fe(IO_3)_3$, N-(4-nitrophenyl)-(L)-prolinol, urea, 4-Nitroaniline, 2-Methyl-4-nitroaniline, 3-Methyl-4-methoxy-4'-nitrostilbene), $\beta$-$BaB_2O_4$, $LiB_3O_5$, $KH_2PO_4$, $NH_4H_2PO_4$, $KD_2PO_4$, $CsLiB_6O_{10}$, $KTiOAsO_4$, $LiTaO_3$, $RbTiOAsO_4$, $BiB_3O_6$, $K_2Al_2B_2O_7$, $KBe_2BO_3F_2$, $BaAlBO_3F_2$, $La_2CaB_{10}O_{19}$, $GdCa_{40}(BO_3)_3$, $YCa_4O(BO_3)_3$, $Li_2B_4O_7$, $LiRbB_4O_7$, $RbTiOPO_4$, $KB_5O_8.4H2O$, $CsB_3O_5$, $C_4H_7D_{12}N_4PO_7$, a-$HIO_3$, $LiCOOH.H_2O$, $CsH_2AsO_4$, $CsD_2AsO_4$, $RbH_2PO_4$, $CsTiOAsO_4$, $Ba_2NaNb_5O_{15}$, $K_3Li_2Nb_5O_{15}$, $CO(NH_2)_2$, and $LiIO_3$.

Only specific embodiments of the invention are discussed above and in the examples below, it should be understood that the unique combination of properties possessed by the functionalized second harmonic nanoprobes of the current invention allows for a number of applications including, for example, molecular labeling, protein, DNA, RNA and tumor imaging and cancer or stem cell therapy evaluation and diagnosis as well as quantification in optical imaging. In vivo imaging of biological processes such as cell signaling, neuroimaging, protein conformation probing, DNA conformation probing, gene transcription, and virus infection and replication in cells. In addition the functionalized SHG nanoprobes of the current invention may be used to for a number of (in vivo) imaging applications.

Exemplary Embodiments

The present invention will now be illustrated by way of the following examples, which are exemplary in nature and are not to be considered to limit the scope of the invention.

EXAMPLE 1

Functionalization of $BaTiO_3$

In one exemplary embodiment, $BaTiO_3$ was functionalized in accordance with the functionalization method described above. The specific chemical schematic used in this example is shown in FIG. 6, and described in detail below.

Materials and Methods

Chemicals were obtained from the following sources and used without further purification: barium titanate ($BaTiO_3$, Nanostructured & Amorphous Materials, Inc., 99.9%, 200 nm), N-aminoethyl-2,2,4-trimethyl-1-aza-2-silacyclopentane (Gelest), hydrogen peroxide solution (Alrich, 30%, aq), anhydrous toluene (Aldrich), 6-azidohexanoic acid, biotin-cyclooctyne, Alexa Fluor 488 conjugated streptavidin (Invitrogen, 2 mg/mL), anhydrous dichloromethane (DCM, Aldrich, 99.8%), 1-ethyl-3-(3-dimethylaminopropyl) carbodiimide (EDC, Thermo Scientific), Nhydroxysuccinimide (NHS, Thermo Scientific), methoxy-Poly(Ethylene Glycol)-succinimidyl carboxymethyl (mPEG2k-SCM, Laysan Bio, MW 2,000), acetone 5-(succinimidyloxycarbonyl)-pyridine-2-yl hydrazone (SANH, EMD chemicals), sodium (meta)periodate (NaIO4, Aldrich), sodium sulfite (Aldrich), sodium cyanoborohydrate (Fluka, >95%), ethanolamine (Aldrich), Alexa Fluor 568 conjugated IgG goat anti-rabbit (Invitrogen, 2 mg/mL), 1× phosphate buffered saline (PBS, Thermo Scientific), anhydrous dimethylformamide (DMF, Aldrich).

Surface Activation

The surface of the inorganic oxide was first activated by hydrogen peroxide to expose more hydroxyl groups on the surface. (See, e.g., S. J. Chang, et al., J Colloid Interface Sci 329, 300 (2009), the disclosure of which is incorporated herein by reference.) In this exemplary embodiment this is achieved by dispersing 400 mg of $BaTiO_3$ in a Teflon flask in 25 mL of hydrogen peroxide by sonication in a Branson 5510 sonicator for 20 min. The solution was then heated at 110° C. for 4 hrs under reflux in an argon environment. The hydroxylated barium titanate ($BaTiO_3$—OH) was then cooled to room temperature, and washed by centrifugation at 3202 rcf eight times 5 min each in double distilled and double deionized water at room temperature (rt) until no bubble formation from the decomposition of $H_2O_2$ into water and oxygen gas was detected in solution. The material was then dried overnight under vacuum at rt.

Formation of Functionalization Platform

The functionalization of $BaTiO_3$—OH with n-aminoethyl-2,2,4-trimethyl-1-aza-2-silacyclopentane to obtain an amine-coated surface—serving as a platform for further functionalization—comprised the second modification step. Functionalization was achieved by the ring-opening reaction with hydroxyl groups on the oxide surface driven thermodynamically by the formation of an oxane bond with silicon without byproduct formation resulting in a high density monolayer formation. (See, Petrarch Systems Inc., Silicon compounds: register and review. Petrarch Systems, Bristol, Pa., (1987), pp. 323, the disclosure of which is incorporated herein by reference.) 50 mg of BaTiO3-OH was heated to 150° C. for 4 hrs under vacuum to eliminate all traces of adsorbed water. The powder was cooled to room temperature and purged with argon. 9 mL of anhydrous toluene was added and BaTiO3-OH was dispersed by sonication for 1 minute using a Branson 5510 sonicator. The desired amount of naminoethyl-2,2,4-trimethyl-1-aza-2-silacyclopentane (1, 5 or 10% v/v) was then added to the solution and stirred for 25 hrs in an inert environment at rt. The material was then washed with ethanol by centrifugation (3202 rcf, 5 min, rt) or with 50 kDa centrifuge membrane filters (Millipore). The final wash was performed in water.

As previously discussed, these amine functionalized oxide nanoparticles ($BaTiO_3$—$NH_2$) can be used as a platform for a plethora of different modification routes, three of which will be described in detail, below.

Functionalization of SHG Nanoprobes

PEGylation Modification: The PEG material used for the surface modification of BaTiO3-NH2 in the current example is mPEG2k-COOH, which was obtained from hydrolysis of mPEG2k-SCM for 4 hrs in aqueous solution with stirring at room temperature. The PEG material was washed by dialysis with 1 kDa floating regenerated cellulose membrane against distilled water for a day. The washed product was then freeze-dried under vacuum overnight. 10 mg of $BaTiO_3$—$NH_2$ material was dispersed in 1 mL of anhydrous DCM and 10 mg of EDC and 10 mg of NHS were added along with 30 mg of mPEG2k-COOH for 4 hrs with stirring at rt. The final solution was washed by centrifugation against ethanol twice and finally with water at 8000 rcf, 2 min at rt.

Click Chemistry Modification: In another example, the nanoprobes were modified using click chemistry. In this example, 30 mg of $BaTiO_3$—$NH_2$ was dispersed in 1 mL of DCM and sonicated with a Branson 5510 sonicator. 10 mg of EDC, 10 mg of NHS, 75 mg of 6-azido hexanoic acid were added. The solution was stirred for 4 hrs at room temperature. The powder was washed with ethanol by centrifugation (8000 rcf, 2 min, rt), and the product, azido modified barium titanate ($BaTiO_3$—$N_3$), was washed with water. 4.8 mg of $BaTiO_3$—$N_3$ were then dispersed in 1.5 mL of PBS by sonication for 40 min with a Branson 5510 sonicator. 3 μL of 10 mM biotin-cyclooctyne solution was added to the solution and stirred overnight at room temperature. The product, $BaTiO_3$-biotin, was washed by centrifugation (3202 rcf, 5 min, rt) in PBS. As a final step, Alexa Fluor 488 conjugated Streptavidin (Invitrogen) was added by mixing 10 μL of 2 mg/mL stock solution to the PBS dispersed $BaTiO_3$—Biotin solution and stirring the solution for 1 hr at room temperature in the dark. The powder was washed five times by centrifugation (8000 rcf, 2 min, rt) against water.

Targeted Antibody Modification: In another example the nanoprobes were functionalized for antibody targeting. In this example, 3 mg $BaTiO_3$—$NH_2$ material dispersed in 0.1 M sodium phosphate 0.15 M sodium chloride buffer, pH 7.14, was reacted with SANH (2 mg in 100 μanhydrous DMF) for 1 hr at room temperature. The powder was washed by centrifugation (8000 rcf, 2 min, rt, 3 times). Alexa Fluor 568 conjugated IgG goat anti-rabbit secondary antibody was oxidized for 25 minutes with NaIO4 (2.5 mg in 100 μL water, kept in dark). Sodium sulfite (1 mg) was used to quench the reaction for 5 minutes. The antibody was washed with centrifuge membrane (3 kDa) against 0.1 M sodium phosphate buffer, 0.15 M NaCl, pH 7.14. Hydrazine modified BaTiO3-NH2 was dispersed in 300 μL of water by sonication to which 100 μL of antibody solution was added and stirred in the dark for 2 hrs at room temperature. To stabilize Schifft's bases, 10 μL/mL of 5 M sodium cyanoborohydride solution was added and stirred in the dark for 30 min at room temperature. To block the un-reacted aldehyde sites on the antibody, 50 μL/mL 1 M ethanolamine solution was added and stirred in dark for 30 min at room temperature. The powder was finally washed by centrifugation against water (8000 rcf, 2 min, 3 times).

Chemical Investigation

As controls, the procedures described above were performed in parallel with un-modified barium titanate powder, with hydroxide-modified $BaTiO_3$ and—for the click chemistry modification—with $BaTiO_3$—OH powder. The chemical composition of the crystals was investigated by FT-IR (Nicolet Nexus 470) and TEM (Technai TF30) with EDS capability. Additional instruments that were used include: Nanoject II nanoliter injector (Drummond Scientific Company) for embryo injections, Intertek Listed ultrasonic cleaner (Model: CD-4800) for nanoparticle dispersion, LSM 510/710 (Zeiss) with 2-photon capabilities (Coherent) for 2-photon microscopy, and Lancer Vibratome Series 1000 sectioning system for fixed embryo sectioning. Imaging was carried out in Labtek multi-well coverslip chambers (2- and 8-well) (Nunc International, #1 thickness).

Figure 8:
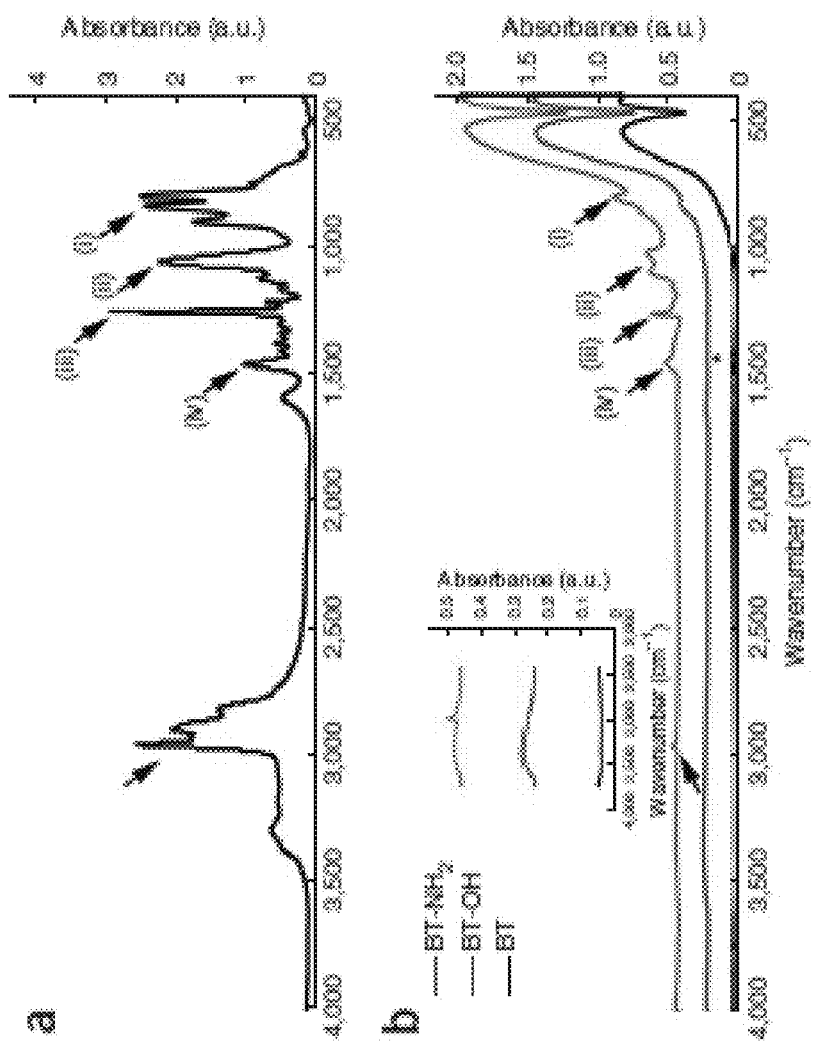
FIG. 8 provides a set of data graphs showing IR analyses characterizing the powders of $BaTiO_3$, $BaTiO_3$—OH and $BaTiO_3$—$NH_2$, where the peaks representing proper silane coating of the surface of $BaTiO_3$—$NH_2$ (middle line) including the 800-$cm^{-1}$ (i), and 1,260-$cm^{-1}$ (iii) stretches corresponding to Si—$CH_3$ bands in the —Si($CH_3$)2O— group within the silane chemical structure, as well as the double-overlapping peak between 1,000 and 1,130 $cm^{-1}$ (ii) corresponding to Si—O—Si absorption, and the peak in the $BaTiO_3$—$NH_2$ data (middle line) near ~1,450 $cm^{-1}$ (iv) corresponds to contributions from the alkane groups in the chemical structure.

To verify the presence of different functional groups on the $BaTiO_3$ surface by means of a rapid spectroscopic technique, FT-IR analysis is performed on $BaTiO_3$, $BaTiO_3$—OH and $BaTiO_3$—$NH_2$ samples using the KBr pellet method (FIG. 8). $BaTiO_3$ and $BaTiO_3$—OH samples were at a concentration of 2 mg within a 47.5-mg KBr matrix, and the $BaTiO_3$—$NH_2$ sample was at a concentration of 3 mg within a 49-mg KBr matrix. As a standard for comparison with $BaTiO_3$—$NH_2$, an IR spectrum (FIG. 8a) was taken of a few drops of N-amino-ethyl-2,2,4-trimethyl-1-aza-2-silacyclopentane coating the surface of an IR film card. The spectrum shows the common peaks for the hydrolyzed silane material as a control (arrows).

The IR spectra (FIG. 8b) for bare commercial $BaTiO_3$ (bottom line), $BaTiO_3$—OH after hydroxylation (middle line) and $BaTiO_3$—$NH_2$ (top line). Here, the dominant peaks in the three $BaTiO_3$ spectra correspond to Ti—O (around 550 cm$^{-1}$) and the Ti—O bend (around 425 cm$^{-1}$). The wide stretch around 3,000 cm$^{-1}$ in the inset of FIG. 8b (middle line) will indicate that $H_2O_2$ treatment hydroxylates the $BaTiO_3$ surface, as expected. The $BaTiO_3$—$NH_2$ sample spectrum (FIG. 8b, middle line) should have Si—$CH_3$ bands at 1,260 cm$^{-1}$ and 800 cm$^{-1}$ from the —O—Si($CH_3$)$_2$— group, along with the overlapping bands at 1,130-1,000 cm$^{-1}$ that are characteristic of Si—O—Si groups introduced in the surface silanization reaction.

After surface functionalization of $BaTiO_3$—$NH_2$ with PEG using an EDC/NHS coupling reaction scheme, salt stability size measurements of the PEG-$BaTiO_3$ can be performed at room temperature in UltraPure water, as well as in 1×PBS solution, to examine surface PEGylation. Particles that are not properly polymer coated should show an increase in nanoparticle size when in salt solution, owing to the shielding of the surface charge by the buffer ions. Dynamic light-scattering analysis should indicate that $BaTiO_3$—OH samples should have a larger hydrodynamic size radius increase over PEG-$BaTiO_3$ samples upon the addition of 11 µl of 10×PBS in 100 µl of solution of PEG-$BaTiO_3$ in water (data not shown). The presence of specific absorptions in the sample is shown in FIG. 8 indicating the presence of —OH groups on the surface of particles for the hydroxylated barium titanate versus the commercial $BaTiO_3$. Similarly, the effectiveness of silanization is indicated by the presence of Si—$CH_3$ bonds on the surface of the nanoparticles.

Figure 9:
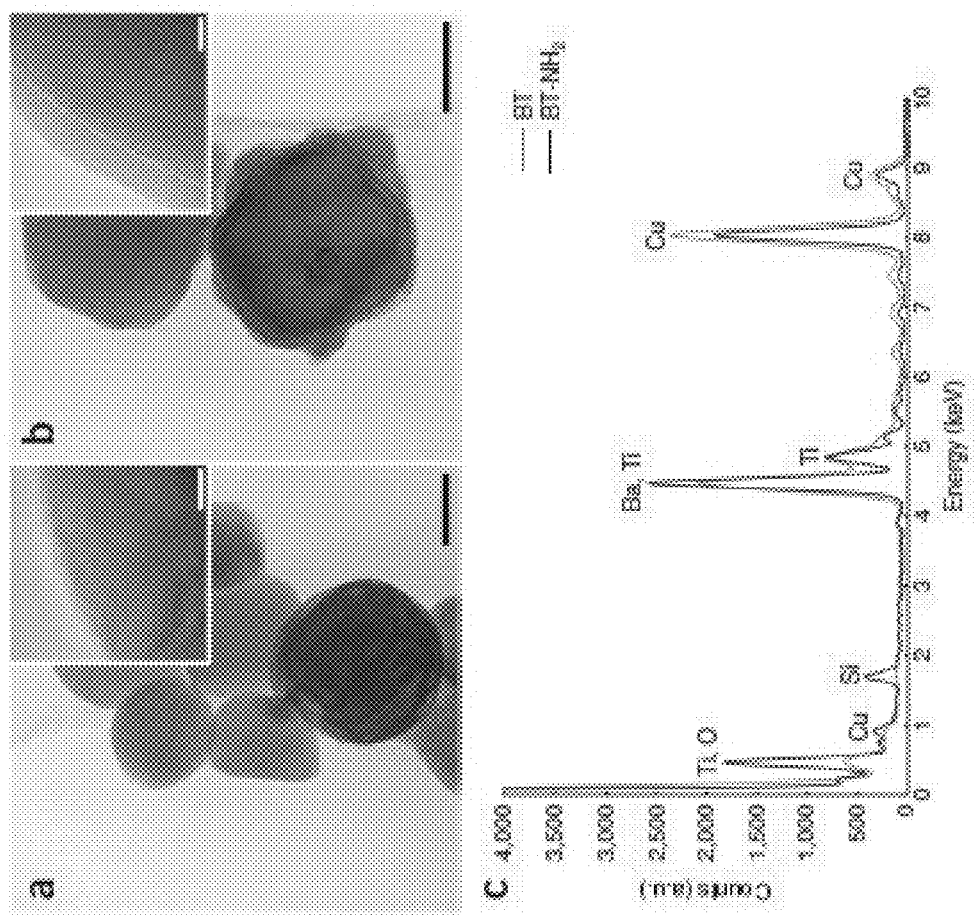
FIG. 9 provides TEM images and EDS analyses confirming surface coating of $BaTiO_3$, where: (a) is a TEM image of nonfunctionalized $BaTiO_3$ control at ×178,600 magnification, as well as at ×4,753,000 magnification (inset); (b) $BaTiO_3$—$NH_2$ at ×136,300 magnification and at ×3,724,000 magnification (inset) showing the presence of an amorphous layer (of variable thickness, usually ~5 nm) around the crystal particle; (c) EDS spectra indicating the atomic composition of nonfunctionalized $BaTiO_3$ nanocrystals and functionalized $BaTiO_3$—$NH_2$ (Scale bars, 100 nm (main figures) and 5 nm (insets). a.u., arbitrary units).

In addition to the FT-IR analysis, TEM images of the $BaTiO_3$ and $BaTiO_3$—$NH_2$ samples are shown in FIGS. 9a and 9b along with the respective EDS analysis (FIG. 8c) for each to demonstrate alternative techniques to assess proper functionalization. TEM images show the morphology of the $BaTiO_3$ and $BaTiO_3$—$NH_2$ nanoparticles and their atomic composition. The presence of an amorphous layer is evident in the $BaTiO_3$—$NH_2$ sample as opposed to the $BaTiO_3$ sample, while both samples still have a crystalline, tetragonal (data not shown here) structure.

EXAMPLE 2

Zebrafish Imaging

In this exemplary embodiment, a protocol for the preparation and use of a particular SHG nanoprobe label, barium titanate ($BaTiO_3$ or BT), for in vivo imaging in living zebrafish embryos was performed. Chemical treatment of the $BaTiO_3$ nanoparticles results in surface coating with amine-terminal groups, which act as a platform for a variety of chemical modifications for biological applications. Here cross-linking of $BaTiO_3$ to a biotin-linked moiety is described using click chemistry methods and coating of $BaTiO_3$ with nonreactive poly(ethylene glycol) (PEG). Details for injecting PEG-coated SHG nanoprobes into zygote-stage zebrafish embryos, and in vivo imaging of SHG nanoprobes during gastrulation and segmentation are also provided.

Methods and Materials

To prepare a 300× Danieau stock solution (which should be diluted to 30× in water before using with embryos), add 34.8 ml of 5 M NaCl, 2.1 ml of 1 M KCl, 1.2 ml of 1 M MgSO4, 1.8 ml of 1 M Ca($NO_3$)$_2$ and 15 ml of 1 M HEPES buffer to 945.1 ml of water. Adjust the pH to between 7.0 and 7.6 with low-molarity NaOH or HCl. The solution can be stored at room temperature for several months.

To prepare a solution of egg water, add 4.5 g of NaCl powder, 1.125 g of CaSO4 powder and 1 ml of methylene blue to 18.9 liters of deionized water. This can be stored at 28° C. (optimal zebrafish embryo incubation temperature) for several months.

To prepare a 0.1% (wt/vol) Tricaine stock solution as follows. Dissolve 50 mg of tricaine powder in 50 ml of 30× Danieau solution (or embryo medium). Adjust the pH to between 7.0 and 7.6 with low-molarity NaOH or HCl. The stock solution can be stored at ~20° C. in 10-ml aliquots for months. Dilute to 0.01-0.02% (wt/vol) when anesthetizing embryos. Tricaine may also be stored at 4° C. for up to 1 week if kept out of light.

For a 25×PTU stock solution, dilute 0.15 g of PTU powder in 200 ml of 30× Danieau solution (or egg water, for embryos that are not being prepared for imaging) and stir for several hours until the powder completely dissolves. The stock can be stored protected from light at 4° C. for several months. Dilute to 1×(0.003% (wt/vol)) when incubating with embryos.

For either regular or low-melting-point agarose, prepare a 1% (wt/vol) stock solution in a heat-safe (and microwave-safe) flask by adding 1 g of agarose powder into 100 ml of 30× Danieau solution and dissolving uncovered on high in the microwave at ~10-s time intervals. Agarose may be stored at RT or in an appropriate incubator (37° C. for low melting point, 65° C. for regular melting point) for at least 1 year as long as no fungal or bacterial growth is seen within the gel. Do not allow the solution to bubble over in the microwave. The agarose should dissolve within 2-3 min, depending on the microwave.

Prepare a plasmid by cloning the cDNA encoding a fluorescent protein of interest into an appropriate vector containing transposable elements flanking the coding region of the plasmid (e.g., pMTB vector44). The DNA injection will allow mosaic fluorescent protein expression within a zebrafish embryo. Tissue-specific promoter-driven expression may be used if labeling of particular tissue types with fluorescence is of interest. In addition, ubiquitous promoters (e.g., β-actin promoter) may be used if cell-specific labeling is not needed.

To prepare transposase mRNA for fluorescent protein genome insertion, generate mRNA encoding the sequence for the transposase that recognizes the transposable elements in the plasmid (e.g., Tol2) by following the manufacturer's instructions in an mRNA expression kit (e.g., mMESSAGE mMACHINE from Ambion).

Toxicity Measurements

To ensure that the inherent toxicity of $BaTiO_3$ was negligible in a biological context, studies were conducted. This issue of labeling probe toxicity cannot be stressed enough; nanoparticles of varying sizes have been shown to be sequestered in the body for long periods of time in the reticuloendothelial system, so decreasing the likelihood of nanoparticle-induced toxicity is of paramount importance to allow these materials to be clinically relevant. To carry out these initial toxicity tests, zygote stage zebrafish embryos were injected with commercially available quantum dots (Invitrogen), $BaTiO_3$, and a 1×PBS control solution to gauge whether early development is affected.

Figure 10:
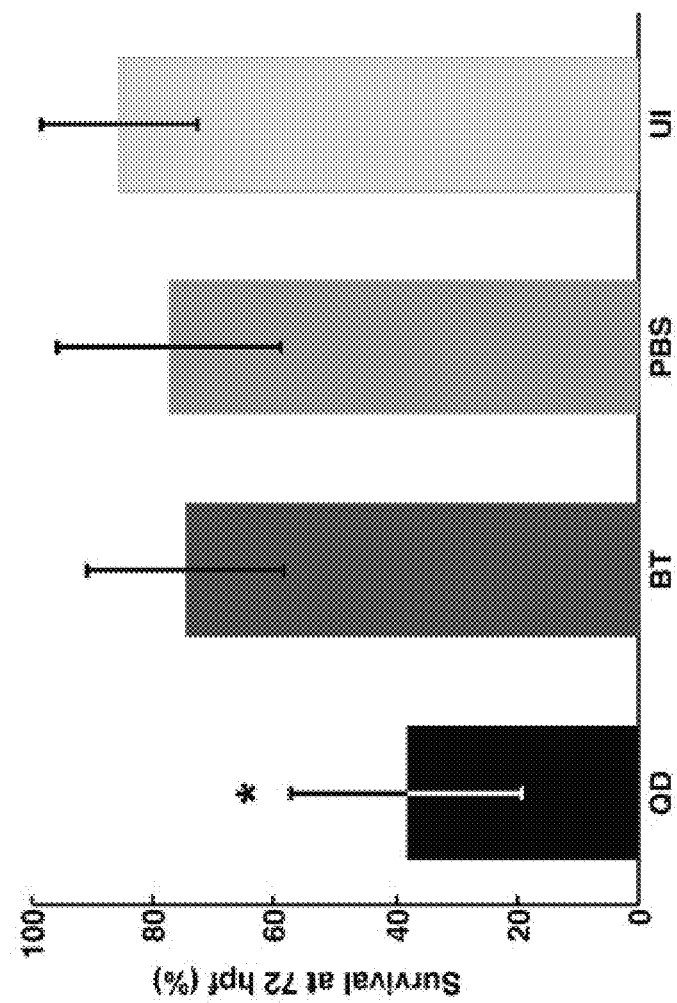
FIG. 10 provides data graphs showing $BaTiO_3$ nanoparticles are nontoxic after zygote stage injections.

These nanomaterials were applied directly into the developing zebrafish and monitored to see whether injected embryos could proceed past the gastrula period, which is a dynamic stage in the zebrafish lifetime where coordinated cell movements, division, and signaling are regulated to set up the initial body plan of the organism. Any dramatic changes in these processes as a result of the injections or the introduction of these nanomaterials could lead to developmental aberrations and embryo lethality. As shown in FIG. 10, data from these preliminary tests suggest that SHG nanoprobe injections are no more detrimental than the control saline injections. In particular, in this experiment, zebrafish were injected at the zygote stage with 2.3 nl of the following: quantum dots (QD), barium titanate nanoparticles (BT), 1× phosphate buffered saline control (PBS, Thermo Scientific), or uninjected control (UI). Embryo lethality was assessed at 72 hpf for each injection condition. Note that this experiment was performed 4 times so that a total of N=110 embryos were analyzed for each injection condition.

An average of 85% of the total embryos were alive from the uninjected control group at 72 hpf, while the $BaTiO_3$ and FSG group had slightly lower survival percentages of 75% and 77%, respectively. The quantum dots had marked reduction in embryo survival, with an average survival percentage of 38%. P values were calculated using an unequal variance, two-tailed t-test. QDs had statistically significant reduction in embryo survival (asterisk) after 72 hpf with respect to all other conditions ($p<10^{-4}$ with respect to $BaTiO_3$ and PBS and $p<10^{-6}$ with respect to UI). $BaTiO_3$ did not have a significant reduction in survival compared to the PBS injection ($p\sim0.7$) or the uninjected control ($p\sim-0.1$), indicating that $BaTiO_3$ toxicity is negligible, even when the material is bare (i.e., not surface functionalized) and injected before a crucial period of early embryo development. Any lethality in the SHG nanoprobe injected embryos likely stemmed from unintentional trauma at the time of injection, which was in marked contrast to the highly toxic quantum dots.

Two-Photon Imaging Experiment: $BaTiO_3$-PEG

In one example, the uptake of the non-toxic nanocrystals functionalized with a non-bioreactive PEG moiety (referred to as $BaTiO_3$—PEG) into cells within a live organism (here: a developing zebrafish embryo) was tested. The functionalized $BaTiO_3$-PEG nanoparticles were sonicated and resuspended in distilled $H_2O$ for 30 min in an ultrasonic cleaner before injecting into the zebrafish embryos. The $BaTiO_3$—PEG solution was diluted 4:5 in 1 µL of Alexa-546 Dextran 40 000MW (Invitrogen) immediately before injection. Zebrafish were injected within 5-10 min of sonication.

Figure 11:
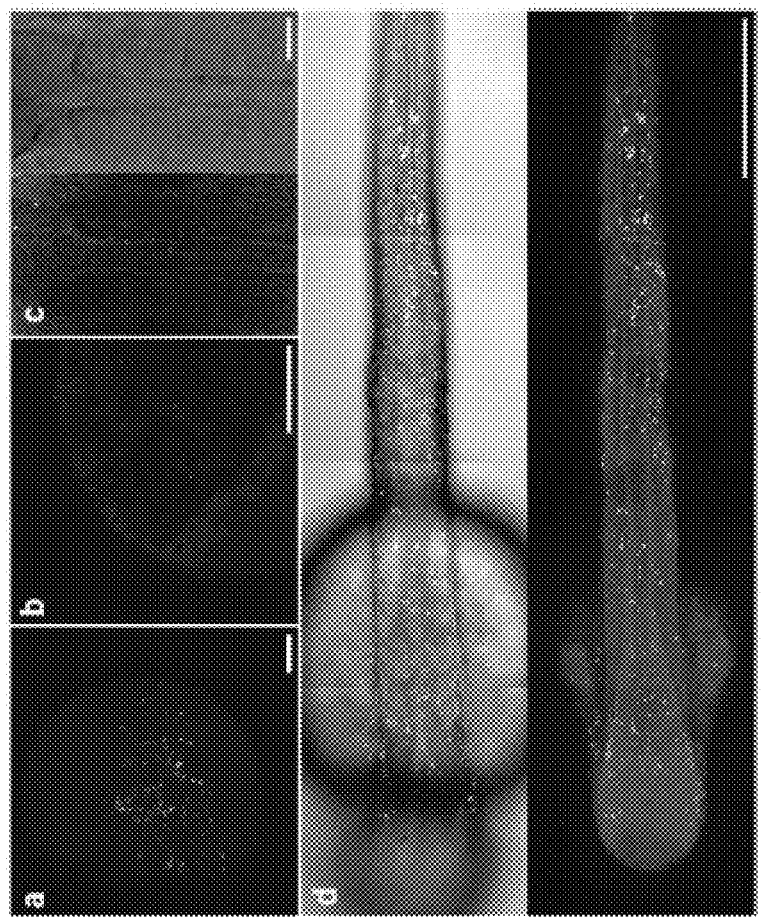
FIG. 11 provides images showing that PEG-$BaTiO_3$ localizes and persists within cells of the developing zebrafish embryo after zygote-stage microinjection: (a) by the sphere stage of development, scattered PEG-$BaTiO_3$ (white) can be seen within a great number of cells in the blastodisc in this surface reconstruction projection; (b) in a single optical slice image of a laterally mounted sphere-stage zebrafish embryo (animal pole is toward the top right, ~40 μm into the embryo in depth), PEG-$BaTiO_3$ (white) can be seen within 6 Bodipy TR methyl-ester-labeled cells; (c) staining with 100 μM Bodipy FL C5 ceramide for 1 h followed by three washes in egg water during the early segmentation (here, the zebrafish was imaged at the 5-somite stage (~12 h after fertilization) in a dorsal orientation (anterior toward the top), which can be best observed in the bright-field channel (right image), while in the left image, PEG-$BaTiO_3$ (white) can be seen within the Bodipy-labeled membrane boundaries of nine cells in various tissue compartments (notochord, somites and neural territories of the developing brain) within a single optical slice ~72 μm deep within the embryo with respect to the dorsal surface; (d) PEG-$BaTiO_3$ (white, top and bottom images) persists within cells throughout the body of the zebrafish even after 24 h of development, as can be seen in this ~48 μm maximum intensity (starting ~50 μm in depth from the dorsal surface) projection of a 100-μM Bodipy TR methyl-ester-stained zebrafish embryo (red, bottom image) (Scale bars, a,b, 100 μm; c, 50 μm; d, 300 μm).
Figure 12:
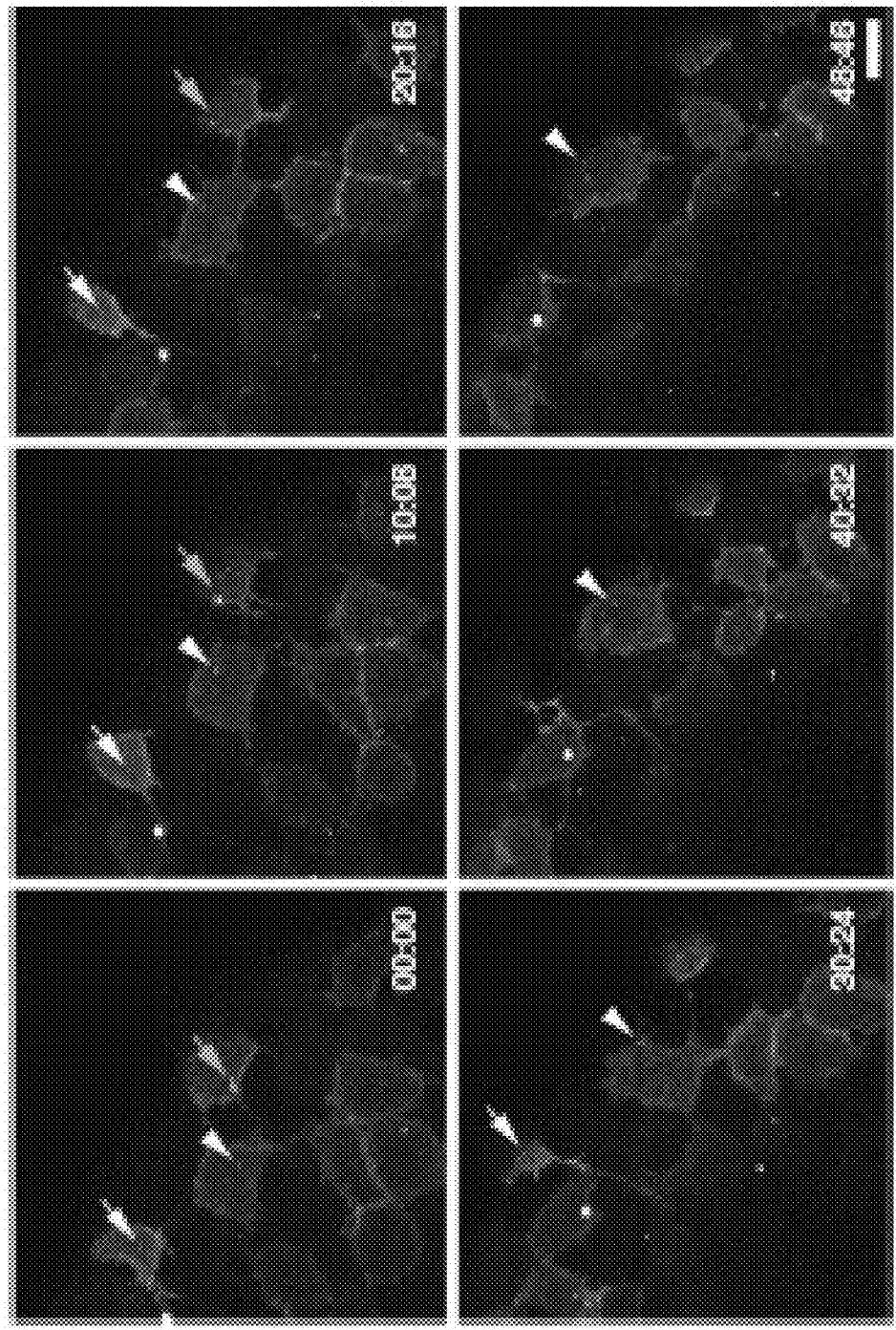
FIG. 12 provides in vivo time-lapse imaging of PEG-BaTiO$_3$ within a zebrafish gastrula embryo. (Three images ~2.5 μm apart in the z-direction were taken of the embryo for each time point with no delay between frames, and a time period of ~38 s was needed to capture each time point. The resulting image stacks were maximum intensity projected in the z-direction. PEG-BaTiO$_3$ (white) nanoprobes can be seen in several Dendra2-labeled, as well as unlabeled, cells. One diffraction limited SHG nanoprobe can be seen within one Dendra2-labeled cell throughout the time-lapse during epiboly migration (arrowheads), whereas other cells containing single SHG nanoprobe clusters move out of the plane of view over time (arrows).) (Time stamps: min:sec. Scale bar, 20 μm.)

Several examples of $BaTiO_3$ imaging within living zebrafish embryos can be seen in FIGS. 11 and 12. In each of these cases, zygote-stage embryos were injected with PEG-$BaTiO_3$ and allowed to develop unhindered in a 28° C. incubator before imaging. Cytoplasmic segregation from the yolk during the zygote stage allows uptake of the crystals into the cells of the embryo early in development. To show that SHG nanoprobes are localized within cells of the zebrafish after yolk cell injection, various dye markers can be used to label the cells within the embryo.

By the late blastula period into early gastrulation, a number of SHG nanoprobes can be seen scattered within the blastodisc, the pile of cells sitting atop the yolk cell that will eventually form the body of the zebrafish (FIG. 11a). On separate occasions, PEG-$BaTiO_3$ was injected into zebrafish zygote-stage embryos, this time with subsequent intracellular dye labeling (FIG. 11b). Even after ~12 h of development, the SHG nanoprobes are still localized and visible inside the cells of the embryo (FIG. 11c), as expected. Note that although many PEG-$BaTiO_3$ clusters can be seen in cells within the embryo, gastrulation still proceeds to completion, which is an important indication that $BaTiO_3$ is a nontoxic labeling probe. SHG nanoprobes can be seen throughout the zebrafish embryo even ~24 h after injection at the zygote stage (FIG. 11d). Notably, any or all of the numerous SHG nanoprobes within the zebrafish cells may be used to track cells in time and space throughout any stage early in development without loss of signal from photobleaching or blinking.

To demonstrate in vivo time-lapse imaging of the SHG nanoprobes within living zebrafish embryos, fluorescent protein and SHG nanoprobe imaging was used in tandem (FIG. 12). At the zygote stage, simultaneous injections of 20 ng µl$^{-1}$ membrane-targeted photoconvertible fluorescent protein Dendra2 plasmid DNA and 80 ng µl$^{-1}$ Tol2 transposase mRNA were administered to label the embryo in a mosaic manner along with PEG-$BaTiO_3$. FIG. 12 shows snapshots from an ~48-min time lapse during late-stage gastrulation, in which single SHG nanoprobe clusters can be seen within at least three Dendra2-labeled epiblasts as the cells migrate across the surface of the embryo. Note that the two labels work well together—mosaic Dendra2 fluorescence allows visualization of membrane dynamics and morphology, whereas SHG from the SHG nanoprobes enables interrogation of intracellular dynamics and cytosolic fluidity. In addition, several nonfluorescent cells are presumably labeled with SHG nanoprobes and can be seen during the time lapse, as these SHG nanoprobes move across the surface of the embryo at rates similar to the other labeled cells in the image. Perhaps most importantly, these SHG nanoprobes are high-contrast labels that will not overlap in space when labeling even adjacent cells (unlike ubiquitous cytosolic fluorescence, for example), and thus they will be especially useful for tracking co-labeled cells in time in three dimensions as the embryo develops, as well. Note that even at illumination wavelengths below the tissue damage threshold, SHG nanoprobes can be seen in time with high contrast without the worry of bleaching or blinking.

EXAMPLE 3

$BaTiO_3$-Biotin Functionalization

Figure 13:
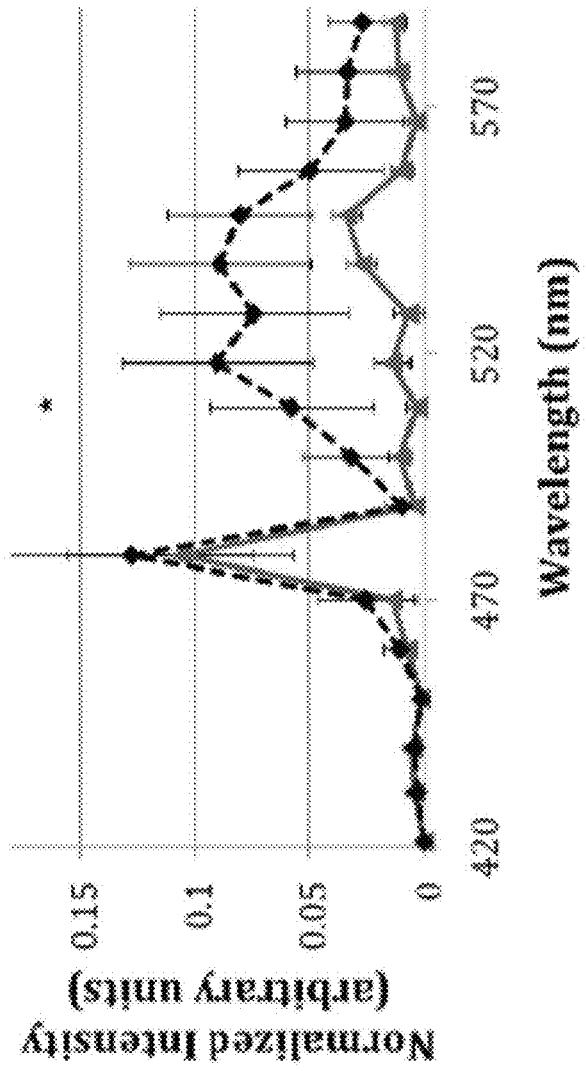
FIG. 13 provides a data graph of click chemistry functionalization versus control by spectral co-localization, where the BaTiO$_3$-biotin (dashed line, average of 25 BaTiO3-biotin SHG nanoprobe clusters) conjugated to AF-488-linked streptavidin maintains strong binding even after 5 washes in DI H$_2$O as indicated by the AF-488 peak at ~519 nm, whereas BaTiO$_3$—OH (solid line, average of 25 BaTiO$_3$—OH SHG nanoprobe clusters) incubated with AF-488-linked streptavidin cannot maintain a strong association as indicated by the lack of an AF-488 nm peak at ~519 nm, showing that proper functionalization is necessary for targeted linkage to the streptavidin protein.

To test for proper functionalization of the barium titanate conjugated to biotin using click chemistry, the $BaTiO_3$-biotin was first bound to Alexa Fluor (AF) 488 dye-linked Streptavidin as mentioned above. Then, using centrifugation, the $BaTiO_3$-biotin and $BaTiO_3$—OH control solutions were washed 5 times with DI $H_2O$ to remove any excess AF-488-linked Streptavidin that was not tightly bound (i.e. that was not bound to biotin, which is a high-affinity binding partner of streptavidin). A drop (~200 µL) of the washed $BaTiO_3$—Biotin conjugated to AF-488-linked Streptavidin was placed in one well of an 8-well coverslip chamber and a drop (~200 µL) of the washed control $BaTiO_3$—OH solution was placed into a second adjacent well. Crystals that sedimented near the coverslip were imaged at an illumination wavelength of 965 nm. By taking spectral data over a wide wavelength range (421 nm-587 nm), co-localization of Alexa-488 signal could be seen with properly functionalized $BaTiO_3$ but not with the $BaTiO_3$—OH control (FIG. 13), indicating that the streptavidin does not nonspecifically adsorb to the $BaTiO_3$—OH surface with high affinity. Thus, the $BaTiO_3$—Biotin was shown to be functionalized properly, and the exposed biotin group retains its ability to bind to streptavidin with high affinity.

EXAMPLE 4

$BaTiO_3$-Antibody Functionalization

Figure 14A:
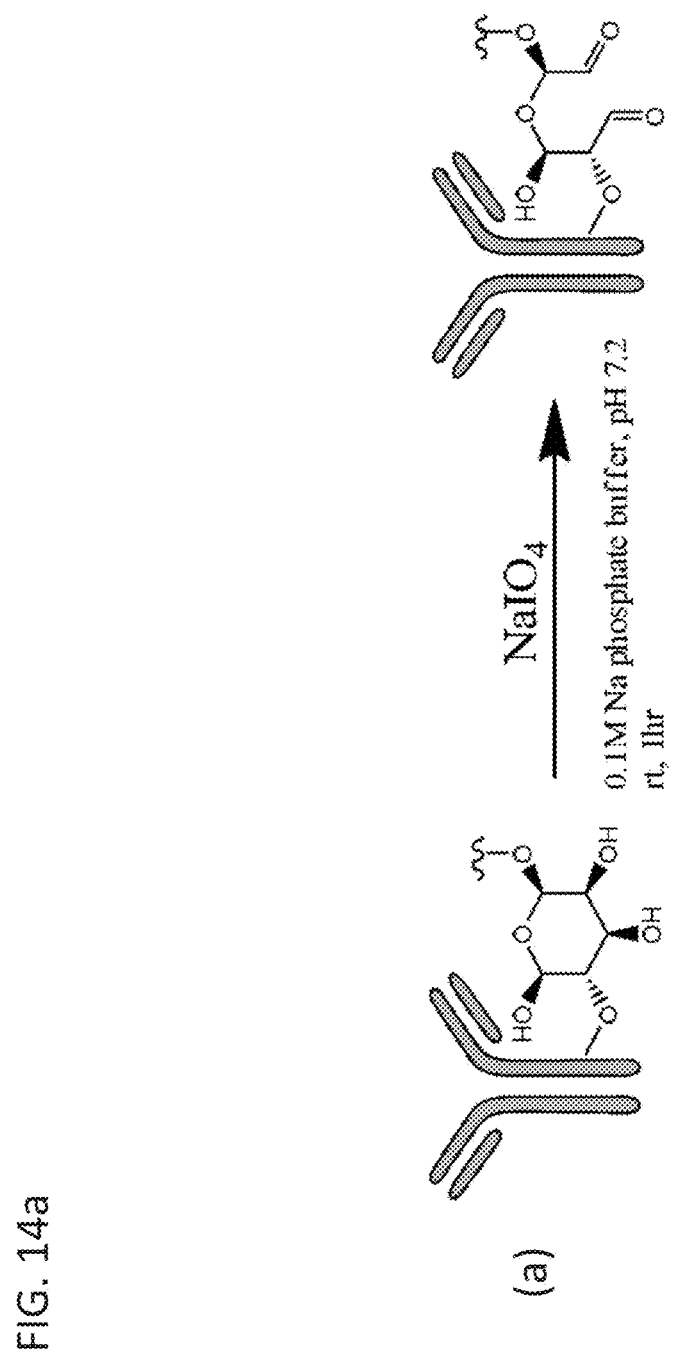
FIGS. 14a and b provide schematic representations of the BaTiO$_3$ surface functionalization with specifically targeting glycosylated IgG antibody, where.
Figure 14B:
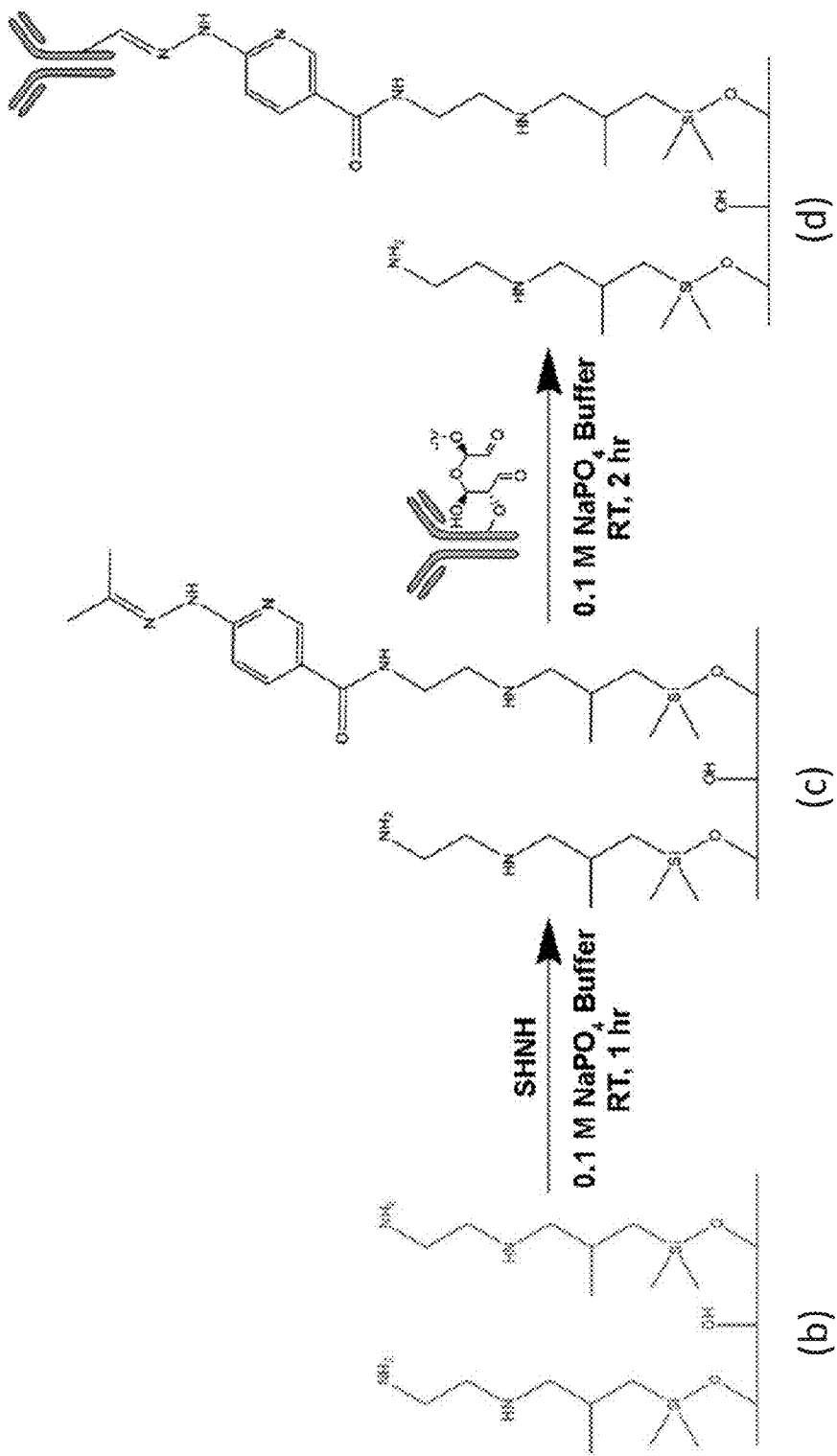
FIG. 14b shows the surface of BaTiO$_3$—NH$_2$ (b) is modified with SHNH reagent, exposing hydrazine functional groups on the barium titanate surface (c), the aldehyde functional groups react with hydrazine moieties forming a specifically targeted coating on the barium titanate surface (d).

Functionalization of barium titanate with antibodies was performed for specific targeting of structures of interest within the organism. Glycoproteins, biological molecules that contain polysaccharide-decorated amino acid chains, can be modified specifically at the sugar residues to produce reactive functional groups. One subset of glycoproteins important in the immune response in mammals, immunoglobulin G (IgG) antibodies, can be divided into two regions in its schematically drawn 'Y' shaped tertiary structure. The first region, comprised of the 'arms' of the Y, is the fragment of the antibody that specifically binds to the antigen and is called Fab (fragment, antigen binding) region. The second region, comprised of the 'base' of the Y, is called the Fc (fragment, crystallizable) region. Polysaccharide chains in the IgG are normally only found in the Fc region of the antibody in mammals, far from the active binding sites. Therefore, by oxidizing the sugar residues on the Fc region, one can produce reactive aldehyde groups and utilize them for site-specific conjugation of SHG probes to the antibody, as schematically described in FIGS. 14a and b.

The general procedure used for antibody targeting is to disperse 10 mg of $BaTiO_3$—$NH_2$ in 0.1 M sodium phosphate 0.15 M sodium chloride buffer, pH 7.14 by sonication for 30 min. The nanoparticles are reacted with 2 mg of succinimidyl 2-hydrazinonicotinate hydrochloride (SHNH) in 100 μL anhydrous BMF for 1 hr at room temperature. The powder was washed by centrifugation in buffer 3 times. Alexa Fluor 488 conjugated IgG goat anti-rabbit secondary antibody was oxidized for 25 minutes with sodium periodate $NaIO_4$ (2.5 mg in 100 μL water, kept in the dark). Sodium sulfite was used to quench the reaction for 5 minutes. The antibody was washed with centrifuge membrane (3 kDa) against 0.1 M sodium phosphate buffer, 0.15 M NaCl, pH 7.14. Hydrazine modified $BaTiO_3$—$NH_2$ was dispersed in 300 μL of water by sonication to which 100 μL of antibody solution was added and stirred in the dark for 2 hrs at room temperature. To stabilize Schifft's bases, 10 μL/mL of 5 M sodium cyanoborohydride solution was added and stirred in the dark for 30 min at room temperature. To block the unreacted aldehyde sites on the antibody, 50 μL/mL 1 M ethanolamine solution was added and stirred in the dark for another 30 min at room temperature. The powder was finally washed with a centrifuge membrane (300 kDa) against buffer.

Figure 15:
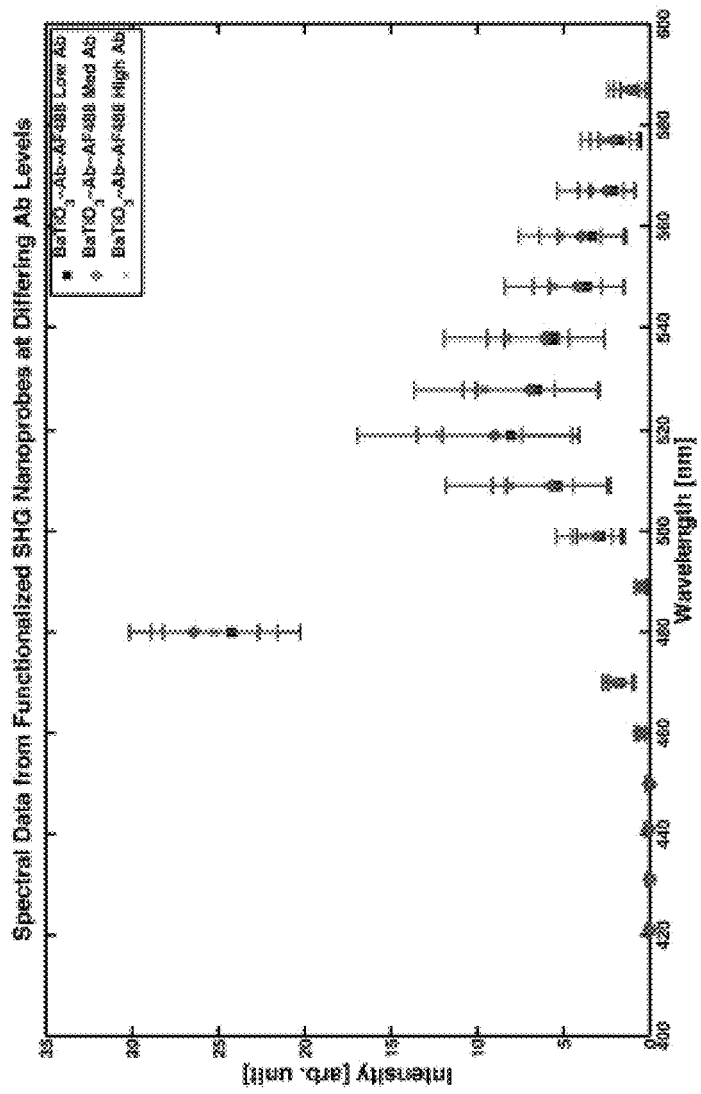
FIG. 15 provides a data plot showing results where the barium titanate surface was coated with AF 488-conjugated IgG antibody with varying concentrations of oxidized antibody.

To test for the proper functionalization of the antibody-conjugated $BaTiO_3$ SHG nanoprobes (referred to as $BaTiO_3$-Ab), antibody-coated $BaTiO_3$ nanoparticles were analyzed for the colocalization of SHG signal by confocal and SHG microscopy. FIG. 15 indicates the colocalization of fluorescent dye and SHG nanoprobe signal for each of the different concentration of AlexaFluor conjugated IgG antibodies that were oxidized by sodium periodate and reacted with hydrazine-coated $BaTiO_3$. This co-localized signal within the wide spectrum of imaging (421 nm to 723 nm) indicates the proper functionalization of the crystal with the antibody. Moreover, the data indicates that the colocalization of the SHG and fluorescent signal is stable for several weeks when stored at 4° C. in 1×PBS.

Zebrafish Imaging

In the second experiment, the efficacy of $BaTiO_3$-Ab targeting was tested, performing immunohistochemistry on fixed zebrafish embryos. In this case, positive Tg(flk1:EGFP) s843 embryos at 2 days post fertilization were dechorionated fixed in 4% paraformaldehyde for 1.5 hours at room temperature. Fish were washed twice (~20 min each) in 1× phosphate buffered saline (PBS) without Ca2+/Mb2+ before embedding the embryos in 4% agarose. Embryos were sectioned to a thickness of ~400 μm before immunostaining. After sectioning, the zebrafish sections were placed in glass hemisphere wells in 500 μL of 1×PBS+0.5% TritonX-100+0.5% bovine serum albumin (BSA) for 30 min on an orbital shaker. 1 μL of primary antibody (rabbit-anti-GFP, Invitrogen) was added and the sections continued to rotate on the orbital shaker for 1.5 hours. The primary antibody was washed 2 times (~10 min each) in 1×PBS. Then, 100 μL of concentrated $BaTiO_3$-Ab (secondary antibody: goat-anti-rabbit conjugated to AF-568, Invitrogen) was diluted in 100 μL 1×PBS+0.5% TritonX-100+0.5% BSA and added onto the sections. The sections in this solution were rotated on the orbital shaker for another 2 hours before washing once for ~10 min in 500 μL 1×PBS. Sections were placed between #1 thickness coverslips before imaging.

Figure 16:
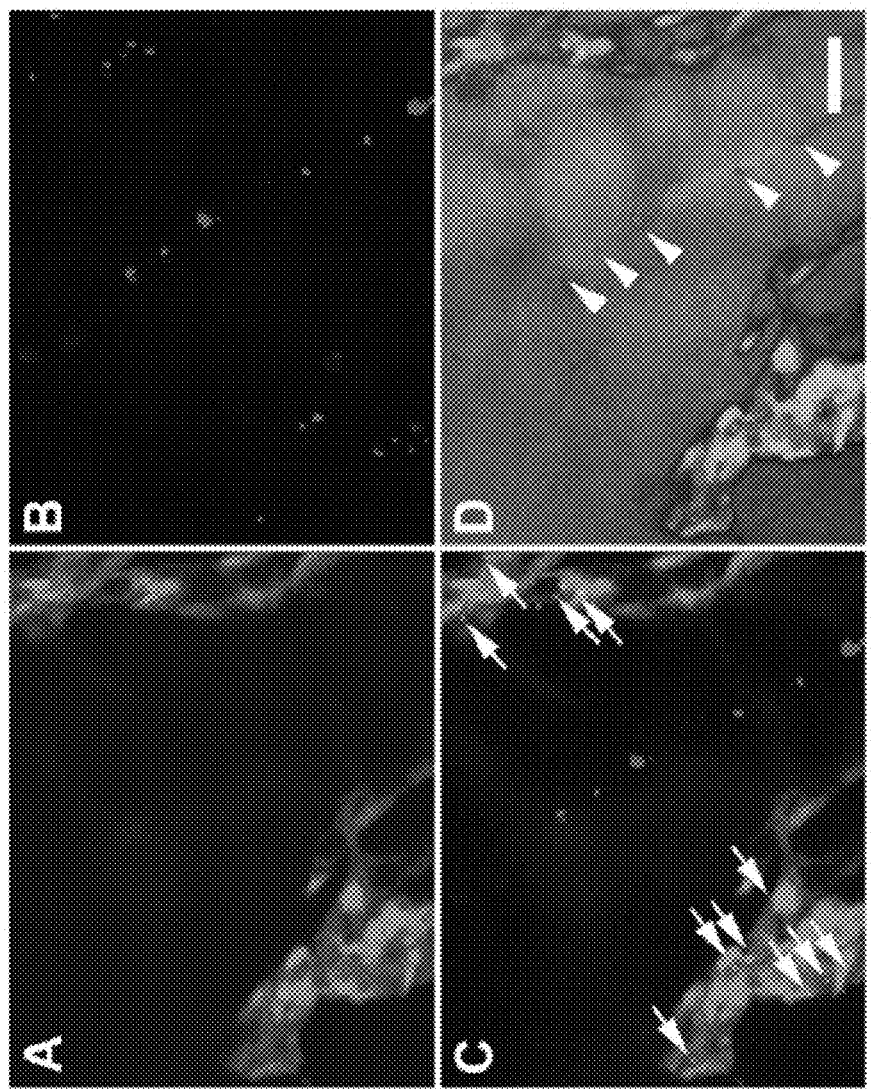
FIG. 16 provides images of co-localized GFP and Ab-BaTiO$_3$ signals in tissue sections show incomplete staining of Ab-BaTiO$_3$, where: (A) GFP fluorescence and (B) SHG from the Ab-BaTiO$_3$ could be seen within the zebrafish tissue after fixation and immunostaining, in this example in the developing forebrain of the zebrafish (anterior mount), (C) Ab-BaTiO$_3$ and GFP had co-localized signal (arrows), though the labeling of the secondary Ab-conjugated BaTiO$_3$ was sparse after the 1.5 hr incubation, and (D) a subset of large (>1 μm) Ab-BaTiO$_3$ clusters appeared stuck within folds of the developing forebrain (bright field in grayscale), even after washing (arrowheads). (Scale bar: 25 μm)(In these images 36 hpf Tg(flk1:EGFP) zebrafish were fixed in 4% paraformaldehyde (PFA) for 1 hr at RT and were washed three times, followed by vibratome (Vibratome Series 1000, The Vibratome Co.) sectioning (200 m thickness) after embedding in 4% agarose (Invitrogen). Primary rabbit anti-GFP antibody (1:500 dilution) was incubated with the sections for 1.5 hr at RT, followed by washing and subsequent (goat anti-rabbit-AF568, Invitrogen) secondary Ab-BaTiO$_3$ incubation (1:4 dilution) for 1.5 hr at RT. Note that the incubation solution was 1×PBS+0.1% Triton X-100+0.5% BSA.)

In an effort to make the Ab-$BaTiO_3$ appropriate for a variety of immunohistochemical applications, a secondary antibody (Invitrogen) is chosen as an ideal candidate for surface functionalization. Thus, any properly chosen primary antibody (i.e., derived from a compatible host for the secondary antibody) could be used to probe the tissue sample, followed by incubation with the secondary Ab-$BaTiO_3$ to achieve high-contrast labeling. Initially, the GFP protein in GFP-labeled endothelial cells was chosen from Tg(flk1:EGFP) transgenic zebrafish. This way, it would be possible to simultaneously view the fluorescence from the GFP-labeled cells along with the SHG from Ab-$BaTiO_3$ to see whether the immunohistochemical labeling was specific or not. So, Ab-$BaTiO_3$ functionalization was tested in fixed vibratome sections of 1.5 dpf embryos, as shown in FIG. 16.

Figure 17:
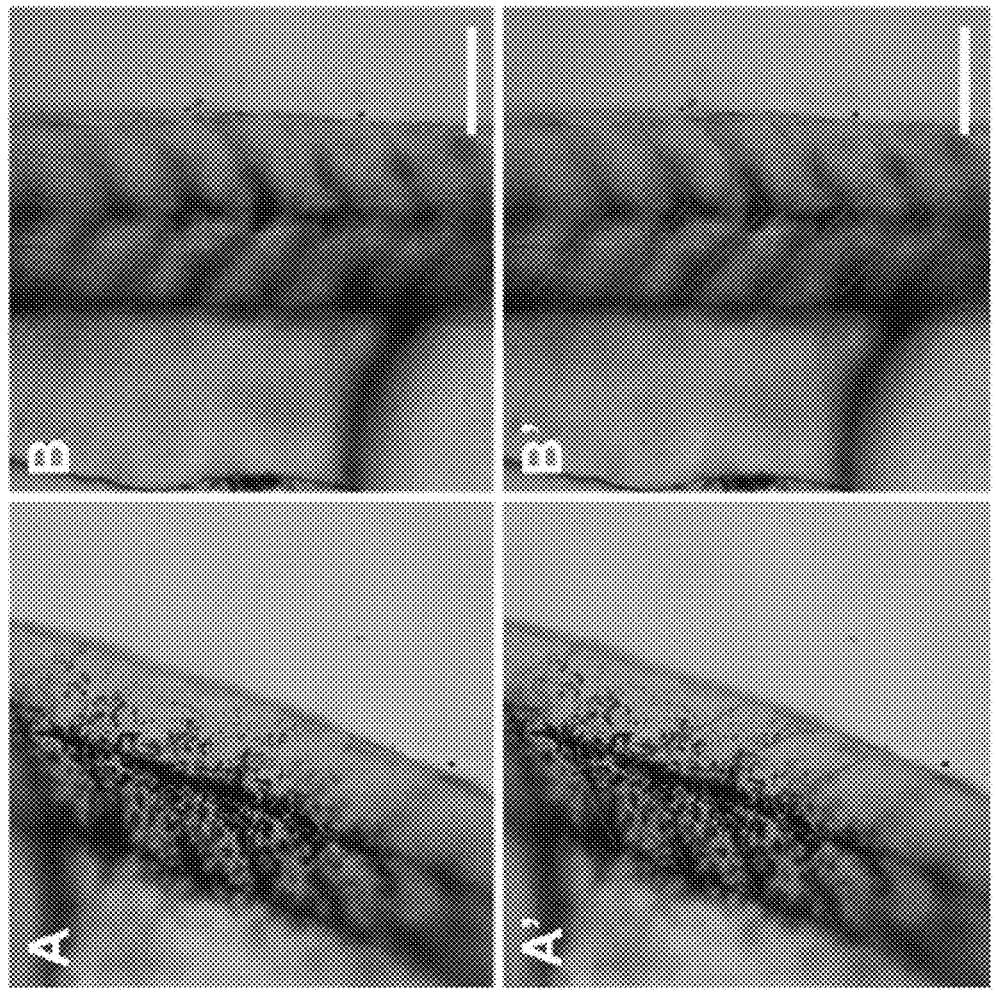
FIG. 17 provides images of Ab-BaTiO$_3$ accumulating at the vertical myosepta when probing for the dystrophin protein, where: (A, A') in this orientation towards the surface of the tissue (anterior top, ventral left), significant accumulation of the nanoprobes can be seen within the vertical myosepta (lines, A') as well as in other nonspecific areas of the somites (especially towards the center, at the horizontal myoseptum), and (B, B') In this orientation deep in the tissue (anterior bottom, ventral left), significant accumulation can be seen predominantly in the vertical myosepta (red lines, B'). (Scale bar: 100 μm)(In these bright field images show a single fixed, 2.5 dpf embryo in two different lateral orientations. Embryos from this trial were prepared as in FIG. 5.15, except that the secondary Ab-BaTiO$_3$ incubation was a 1:3 dilution in PBSTB and went for 3 days in an orbital shaker at 4° C. before minimal washing.)

Interestingly, there was some co-localized SHG and GFP signal (FIG. 16, arrows) a few tens of microns into the tissue. However, penetration into the tissue was limited after 1.5 hr incubation, which resulted in incomplete staining. Thus, initial attempts at Ab-$BaTiO_3$ staining were promising. Subsequently, an alternative epitope was labeled (mouse anti-dystrophin MANDRA1, Developmental Studies Hybridoma Bank), which is an easier target for the Ab-$BaTiO_3$: the protein target, dystrophin, is localized to cell periphery at the vertical myosepta within zebrafish somites and these protein levels are not nearly as excessive as with promoter induced overexpression, as in the Tg(flk1:EGFP) transgenic line. After a three day incubation with the secondary Ab-$BaTiO_3$, significant accumulation of the nanoparticles could be seen within the tissue (FIG. 17A & B), especially at the vertical myosepta (outlines in FIG. 17A' & B'). However, near the surface, there was significant nonspecific binding within the somites, presumably due to Ab-$BaTiO_3$ aggregates getting stuck within pores created by the PBSTB incubation solution.

Figure 18:
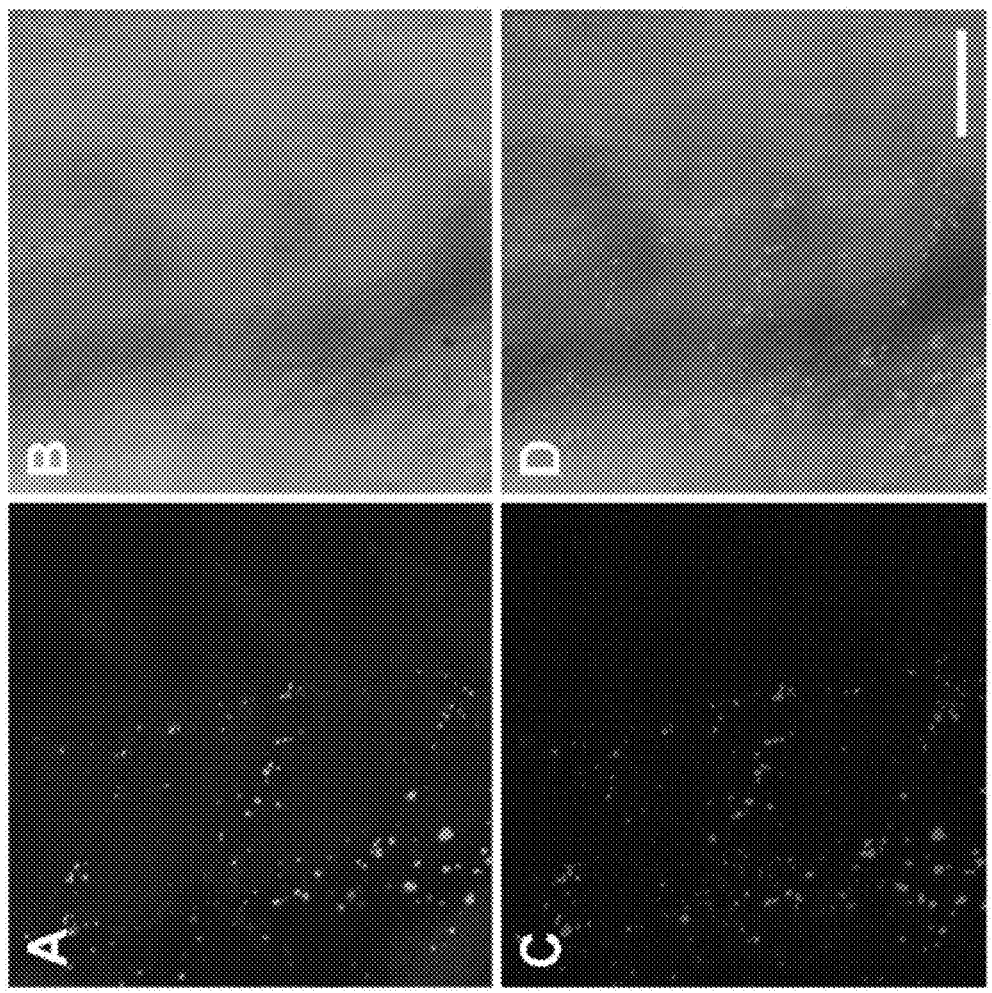
FIG. 18 provides images of higher magnification visualization of a whole-mount stained zebrafish using Ab-BaTiO$_3$, where: (A) AF488 signal from the Ab-BaTiO$_3$ (green) shows significant accumulation of properly functionalized Ab-BaTiO$_3$ at the vertical myosepta, (B) the bright field (grayscale), showing the vertical myosepta more clearly, (C) SHG (contrast enhance in Adobe Photoshop CS3) from the Ab-BaTiO$_3$ showing SHG nanoprobes both inside and outside of the expected localization region at the vertical myosepta, and (D) merge of panels B and C. (Scale bar: 50 μm)(In this MIP image (consisting of 17.6 μm in depth) of a different 2.5 dpf embryo than in FIG. 18, but prepared in the same manner (anterior down, ventral left). This is a zoomed in image (effective 40×: zoom of 2 using a 20×0.8NA air objective, Zeiss) showing the accumulation of Ab-BaTiO$_3$ within fixed zebrafish tissue.)
Figure 19:
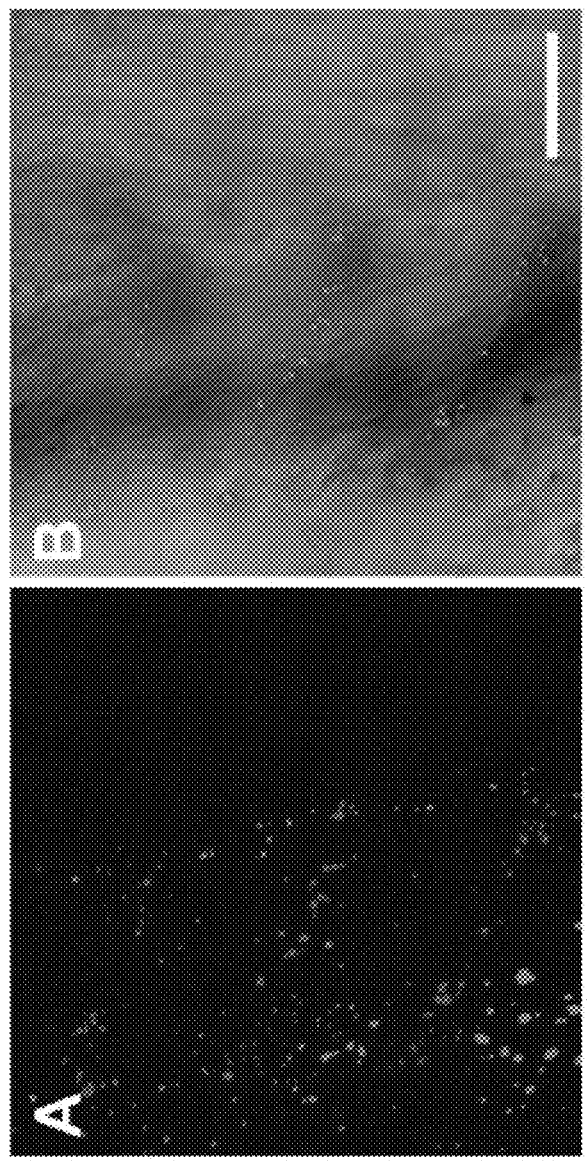
FIG. 19 provides images of Ab-BaTiO$_3$ accumulates mainly in the vertical myosepta and the yolk, where: (A) SHG from Ab-BaTiO$_3$ within the vertical myosepta (red) was isolated from signal from those that were nonspecifically bound (gray). Note that most of the nonspecific binding seen in these images occurs within the yolk (towards the left side of the image), where nonspecific binding is often significant and difficult to block with BSA, and (B) labeled Ab-BaTiO$_3$ from panel A was isolated from the rest of the SHG signal in the tissue and superimposed on the grayscale bright field image from FIG. 19B to appreciate co-localization at the three visible vertical myosepta. (Scale bar: μ50 m)(This figure is a more processed version of the zoomed image seen in FIG. 19.)

Zooming into the tissue and visualizing the AF488 signal conjugated to the secondary Abs atop the $BaTiO_3$ provides more context into why nonspecific binding may occur (FIG. 18). $BaTiO_3$ that has co-localized AF488 fluorescence and SHG predominately localizes at the vertical myosepta (see AF488 signal on SHG nanoprobes in FIG. 18A), while $BaTiO_3$ without appreciable AF488 signal can be seen in other portions of the muscle compartment and the yolk (toward the left side of the image in FIG. 18). This separation between specific and non-specific labeling can be more clearly appreciated in FIG. 19A, where SHG nanoprobes along the vertical myosepta are labeled in bright spots and the nonspecific binding $BaTiO_3$ is labeled in gray. Interestingly, a rough calculation of this particular image shows that approximately half of the $BaTiO_3$ seems to localize at the three visible myosepta, while the remaining half accumulates nonspecifically, especially within the yolk (towards the left side of the image). It is important to note that yolk accumulation is somewhat expected, because of the high lipid content in this tissue compartment.

Live Mouse Bone Marrow Cells

Following the fixed Ab-$BaTiO_3$ tests, live primary cells in suspension were targeted. To accomplish this, whole bone marrow was isolated from two freshly killed mice by flushing the marrow from the humerus and tibia bones from each mouse with media (using a syringe). Then, the cells were affinity purified for the cKit (CD117) marker, which has been shown to target hematopoietic stem and progenitor cell populations, by running cells incubated with anti-CD117-conjugated magnetic beads through a column. Cells were then split into two equal volumes and were incubated with either $BaTiO_3$—OH solution in 1× Hank's balanced salt solution (HBSS, Invitrogen) or Ab-$BaTiO_3$ (monoclonal IgG, FITC rat anti-mouse Ly-6A/E, BD Biosciences) solution in 1×HBSS for 15 min on ice; flicking of the tube every 3 minutes kept the particles and cells in suspension during the incubation. After incubation, cells were separated from unbound SHG nanoprobes by centrifugation. Briefly, cells in medium (4 mL of HBSS) were carefully layered over lymphocyte separation medium (4 mL, Cellgro by Mediatech, Inc.) and were centrifuged at 400 g for 5 min. After centrifugation, excess $BaTiO_3$ pellets at the bottom of the tube, while cells remain at the media interface. Cells were carefully pipetted and resuspended in 4% formalin followed by imaging the same day in 8-well coverslip chambers 4.

Figure 20:
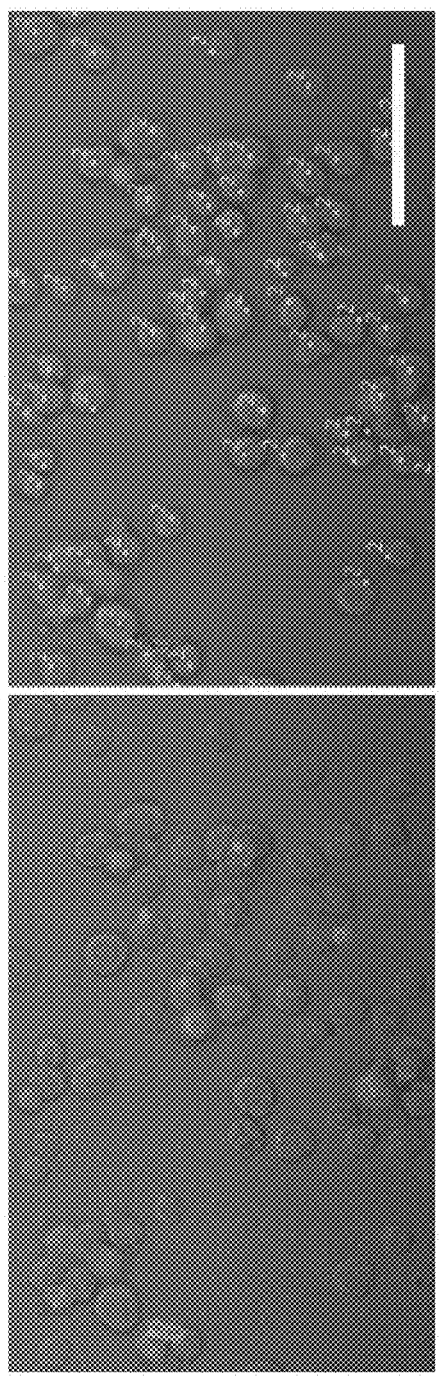
FIG. 20 provides images of the binding of BaTiO$_3$—OH to isolated primary mouse marrow cells, where: (Left panel) this is a zoomed portion of a merged image of SHG from BaTiO$_3$—OH (spots) and a bright field image of the cKit enriched primary cells (grayscale), and (Right panel) cells were counted (labeled with "2") using the "cell counter" plugin for ImageJ, additionally, some cells were associated with BaTiO$_3$—OH (labeled with "1") even after centrifugation in lymphocyte separation medium. (Scale bar: 50 μm)(In this experiment, bone marrow cells were isolated from freshly euthanized mice and cKit enriched using an affinity column, resulting in a population of predominately mononuclear cells. Half of these cells were incubated for 15 min on ice (to limit fluid phase endocytosis) with BaTiO$_3$—OH before being spun down for 5 min at 400 g in lymphocyte separation medium (Cellgro by Mediatech, Inc.) to isolate the cells from unbound BaTiO$_3$—OH. Cells were then immediately fixed in 4% formalin and imaged in an 8-well coverslip chamber (Nalge Nunc International) on a laser scanning microscope (Zeiss) with an LD C-Apochromat 40×/1.1 NA water objective (Zeiss).)
Figure 21:
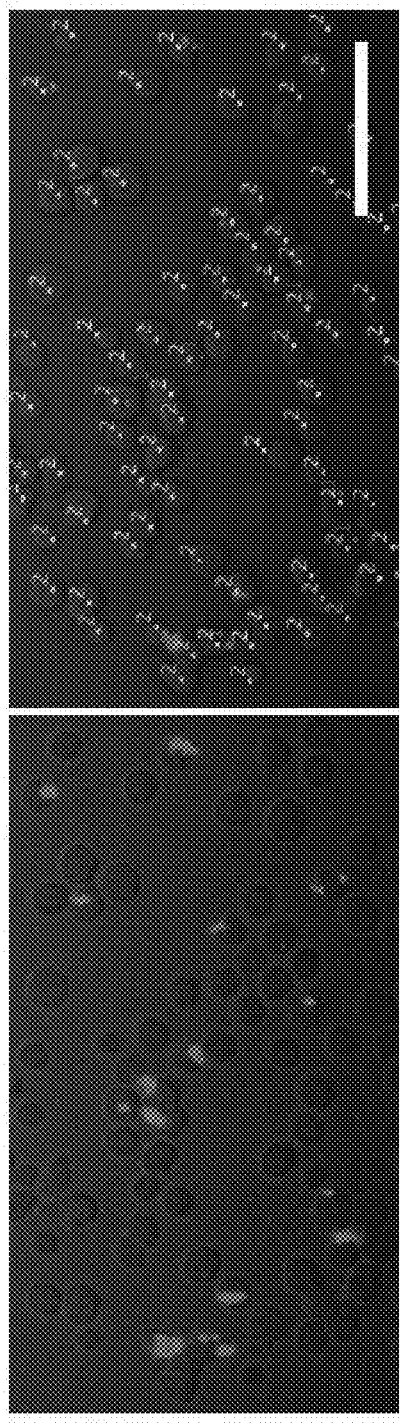
FIG. 21 provides images of binding of Ab-BaTiO₃ to isolated primary mouse marrow cells, where: (Left panel) this is a zoomed portion of a merged image of SHG from Ab-BaTiO₃ (bright spots) and a bright field image of the cKit enriched primary cells (grayscale), and (Right panel) cells were counted (labeled with "2") using the "cell counter" plugin for ImageJ, and additionally, Ab-BaTiO₃ was bound to a number of the cells on the plate (labeled with "1") even after centrifugation in lymphocyte separation medium. (Scale bar: 50 μm)(For these images, an equal aliquot of cKit enriched cells from those prepared in FIG. 21 were incubated for 15 min on ice (to limit fluid phase endocytosis) with Ab-BaTiO₃. In this case, the Ab was a primary Ab directed toward the Sca1 antigen on the surface of a subset of the cKit enriched cells (monoclonal IgG, FITC rat antimouse Ly-6A/E, BD Biosciences). This incubation was followed by a 5 min centrifugation step at 400 g in lymphocyte separation medium to isolate the cells from unbound Ab-BaTiO₃. Cells were fixed in 4% formalin, placed in a well of an 8-well coverslip chamber (Nalge Nunc International) and imaged as in FIG. 21.

It is expected that the Ab-$BaTiO_3$ should be able to target approximately 10% of the cKit enriched population. To test this, 11 independent regions were imaged for each sample ($BaTiO_3$—OH and Ab-$BaTiO_3$). In each of the 11 regions for each sample, cells associated with $BaTiO_3$ were counted along with the total number of cells in the region to determine an average fraction of $BaTiO_3$-bound cells. A picture of zoomed portions of individual regions for $BaTiO_3$—OH and Ab-$BaTiO_3$ can be seen in FIGS. 20 and 21. After counting over $10^4$ total cells, it was determined that Ab-$BaTiO_3$ binds more effectively to the primary cells than the $BaTiO_3$—OH control.

Although one potential antibody functionalization is described above, a possible alternative functionalization could take advantage of $BaTiO_3$-streptavidin, which should allow selective attachment to biotinylated molecules for specific cell targeting—biotinylated antibodies, in this case—as was described previously for quantum dots. In addition, the protocol can potentially be extended to directly conjugate antibodies to the surface through covalent means atop the amine-terminal functionalization platform. More refined $BaTiO_3$ synthesis and adjustment of the Ab:$BaTiO_3$ ratio in the functionalization protocol may provide even better labeling. This demonstrates that Ab-$BaTiO_3$ will be highly suited for live cell imaging approaches. Ab-$BaTiO_3$ can also be used to target specific cells within a heterogeneous population. If Ab-$BaTiO_3$ also bound to these promiscuous binding cells as effectively, it can be estimated that the Ab-$BaTiO_3$ was able to specifically target 8% of the total population, which is in close agreement with the aforementioned expectation that 10% of cKit+ cells express Sca1 on their surface. This result is of great significance—certain specifically labeled Sca1-displaying cells (such as hematopoietic stem cells) can be reintroduced into the bloodstream of a mouse and can home to the bone marrow. Importantly, nonspecific binding to promiscuous binding cells could be avoided altogether by isolating a pure population of cells by FACS sorting (as performed previously to isolate hematopoietic stem and progenitor cells) before the Ab-$BaTiO_3$ incubation. Thus, Ab-$BaTiO_3$-labeled cKit+, Sca1+ cells could potentially be tracked in the highly refractory bone marrow environment or within the vasculature of recipient mice in the future.

SUMMARY

SHG nanoprobes are a class of materials that have great potential in biological applications since they have a tight spectral signal that is compatible with fluorescence-based approaches, can be inherently nontoxic (as is the case with $BaTiO_3$), and can be seen deep within highly refractive tissues. The embodiments described herein have refined $BaTiO_3$ as a biologically relevant imaging probe by creating a robust functionalization protocol, where stable terminal amines serve as a functionalization platform for a variety of chemical additions to the nanoparticle surface. The advantage of the described functionalization routine is that the intermediate step of surface exposed amine-terminal groups acts as a platform for a variety of chemistries, including non-reactive surface coatings (e.g., PEG), bio-orthogonal linkages (i.e., copper-free click chemistry), and protein targeting moieties (IgG antibodies, in this case). Importantly, a majority of the methods used in this functionalization protocol are easily attempted at room temperature (RT) and moderate conditions.

In addition it has been demonstrated that these nanoprobes can be incorporated into an in vivo setting using zygote stage injection of dispersed, PEG functionalized SHG nanoprobes. Over time, the dramatic cell divisions and migration that are hallmarks of early development, cause the SHG nanoprobes to distribute within a large number of cells, and we show how to image these nanoparticles within the developing embryo. The in vivo example illustrates the utility of the SHG nanoprobes: because of the high signal-to-noise ratio (SNR), appreciable brightness, and absence of bleaching/blinking, SHG nanoprobe labeling of cells within a biological tissue of interest will allow for long-term imaging even within challenging (i.e., highly scattering and absorbing) tissue environments. Finally, we demonstrate applications of our antibody (Ab) functionalization in fixed and live cells.

Additionally, a combined fluorescence/SHG imaging-based method has been described to test future functionalization chemistries, in this case with $BaTiO_3$-streptavidin AF488, where it has been shown that this click chemistry-mediated routine results in efficient and significant surface coating of $BaTiO_3$. Furthermore, well-dispersed PEG-$BaTiO_3$ was introduced into live zebrafish embryos and observed their subcellular localization, taking advantage of the high-contrast, non-bleaching, and non-blinking spectral properties of SHG nanoprobes. Finally, Ab-$BaTiO_3$ can be targeted to specific epitopes in both fixed and live samples, giving preliminary insight into how these nanoparticles could be used for specific labeling experiments in the future.

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method of probing structures and biological processes comprising:
   interspersing a functionalized probe nanostructure comprising a nanocrystalline body configured with a biologically relevant functionalization molecule bound to the probe nanostructure through a functionalization platform including a plurality of modifying molecules having amine terminal groups, the modifying molecules being linked to the outer surface of the body through a plurality of hydroxyl molecules, and wherein the nanocrystalline body is formed of a crystal material having an internal crystal structure having a unit cell having no inversion symmetry such that the crystal material generates a second harmonic signal independent of the overall shape of the nanocrystalline body when illuminated by an external excitation source;

the functionalization molecule being selected to target a species of interest, such that the functionalized probe nanostructure interacts with the targeted species of interest;

illuminating the probe nanostructure with an external excitation source; and detecting the second harmonic signal from the nanoprobe.

2. The method of claim 1, wherein the targeted species of interest is selected from the group consisting of an antigen, a peptide sequence, a nucleic acid sequence, RNA, DNA, and a sugar/carbohydrate group.

3. The method of claim 1, wherein the targeted species of interest is indicative of the presence of one of either a specific medical condition or a specific pathogenesis.

4. The method of claim 1, wherein the functionalized probe nanostructure is directly attached to the targeted species of interest through the functionalization molecule.

5. The method of claim 1, wherein the probe nanostructure is conjugated through the functionalization molecule to a probe molecule that is sensitive to the presence of the targeted species of interest.

6. The method of claim 1, wherein the step of illuminating is conducted while the probe nanostructure is external to the source of the targeted species of interest.

7. The method of claim 1, wherein the step of illuminating is conducted while the probe nanostructure is in vivo to the source of the targeted species of interest.

8. The method of claim 7, wherein the signal from the probe nanostructure is utilized to image the specific location of the targeted species of interest within the source of the target of interest.

9. The method of claim 1, further comprising incorporating an exciter nanostructure to the targeted species of interest, said exciter nanostructure designed to produce a resonant electrical field of a specified frequency when exposed to an excitation source, wherein the functionalized probe nanostructure generates a second harmonic resonance emission when brought within range of the resonant electrical field of said exciter nanostructure.

10. The method of claim 1, wherein the excitation source is selected from the group consisting of a two-photon source, a nanosecond pulsed laser, a picoseconds pulsed laser, a femtosecond pulsed laser, and an attosecond pulsed laser.

11. The method of claim 1, wherein the crystal material of the nanocrystalline body is selected from the group consisting of $BaTiO_3$, SiC, ZnO, $LiNbO_3$, $KNbO_3$, $KTiOPO_4$, $Fe(IO_3)_3$, N-(4-nitrophenyl)-(L)-prolinol, urea, 4-Nitroaniline, 2-Methyl-4-nitroaniline, 3-Methyl-4-methoxy-4'-nitrostilbene), $\beta$-$BaB_2O_4$, $LiB_3O_5$, $KH_2PO_4$, $NH_4H_2PO_4$, $KD_2PO_4$, $CsLiB_6O_{10}$, $KTiOAsO_4$, $LiTaO_3$, $RbTiOAsO_4$, $BiB_3O_6$, $K_2Al_2B_2O_7$, $KBe_2BO_3F_2$, $BaAlBO_3F_2$, $La_2CaB_{10}O_{19}$, $GdCa_4O(BO_3)_3$, $YCa_4O(BO_3)_3$, $Li_2B_4O_7$, $LiRbB_4O_7$, $RbTiOPO_4$, $KB_5O_8.4H_2O$, $CsB_3O_5$, $C_4H_7D_{12}N_4PO_7$, a-$HIO_3$, $LiCOOH.H_2O$, $CsH_2AsO4$, $CsD_2AsO_4$, $RbH_2PO_4$, $CsTiOAsO_4$, $Ba_2NaNb_5O_{15}$, $K_3Li_2Nb_5O_{15}$, $CO(NH_2)_2$, and $LiIO_3$.

12. The method of claim 1, wherein the functionalization platform is formed from an amine functionalized reagent selected from the group consisting of N-aminoethyl-2,2,4-trimethyl-1-aza-2-silacyclopentane, 3-aminopropyltriethoxysilane, and 3-aminopropyltrimethoxysilane, N-succinimidyl S-acetylthioacetate, isothiocyanates, acyl azides, N-hydroxysuccinimide esters, sulfonyl chloride derivatives, epoxides, fluorobenzene derivatives, and carbonate compounds.

13. The method of claim 1, wherein the functionalization molecules are bound to the functionalization platform through a linkage selected from the group consisting of mono functional or multifunctional PEGylation, biocompatible polymers, click chemistry, and antibody targeting.

14. The method of claim 1, wherein the functionalization molecule is selected from the group of a non-bio-reactive coating and a bio-reactivity enhancer.

15. The method of claim 1, wherein the bio-reactivity enhancer is a PEG analogue selected from the group consisting of biotin, bromo, amino, aminoethyl, carboxymethyl, succinimidosuccinate, tosylate, mesylate, aldehyde, actadecylamine, monopalmitate, and stearoyloxy derivatives of PEG.

16. The method of claim 1, wherein the functionalization molecule is a glycosylated antibody originating from a host.

17. The method of claim 1, wherein the functionalization molecule is configured to target or label a specific cell, biological molecule or molecule.

18. The method of claim 1, wherein the functionalized probe nanostructure is configured to be acceptable for use in conjunction with a technique selected from the group consisting of SHG imaging, direct nucleic acid sequencing in a Multi-SHG Detection Imaging modality, FRESH, optical monitoring of electric fields, imaging/detecting medical conditions or neoplasm, detection or tracking of therapeutic agents, and rapid detection systems.

19. The method of claim 1, wherein the functionalized probe nanostructure includes a plurality of different biologically relevant functionalization molecules.

20. The method of claim 1, wherein the functionalized probe nanostructure further includes at least one additional linkage between the functionalization platform and a biologically relevant functionalization molecule.

* * * * *